US 8,004,661 B2

(12) United States Patent
Luscher

(10) Patent No.: US 8,004,661 B2
(45) Date of Patent: Aug. 23, 2011

(54) METHOD AND APPARATUS FOR SORTING CELLS

(75) Inventor: Mark Luscher, Toronto (CA)

(73) Assignee: Microbix Biosystems Inc., Mississauga (CA)

( * ) Notice: Subject to any disclaimer, the term of this patent is extended or adjusted under 35 U.S.C. 154(b) by 208 days.

(21) Appl. No.: 12/495,406

(22) Filed: Jun. 30, 2009

(65) Prior Publication Data

US 2009/0325217 A1 Dec. 31, 2009

Related U.S. Application Data

(60) Provisional application No. 61/077,083, filed on Jun. 30, 2008.

(51) Int. Cl.
*G01N 21/64* (2006.01)
*C12M 1/34* (2006.01)
*C12M 1/42* (2006.01)

(52) U.S. Cl. .......... 356/72; 356/318; 356/339; 356/342; 356/419; 422/82.08; 435/288.7; 436/172; 250/461.2

(58) Field of Classification Search ...................... 356/72
See application file for complete search history.

(56) References Cited

U.S. PATENT DOCUMENTS

| | | | |
|---|---|---|---|
| 2,656,508 A | 10/1953 | Coulter | |
| 3,380,584 A | 4/1968 | Fulwyler | |
| 3,497,690 A | 2/1970 | Wheeless, Jr. et al. | |
| 3,657,537 A | 4/1972 | Wheeless, Jr. et al. | |
| 3,710,933 A | 1/1973 | Fulwyler et al. | |
| 4,188,542 A | 2/1980 | Hogg et al. | |
| 4,395,397 A | 7/1983 | Shapiro | |
| 4,629,687 A | 12/1986 | Schindler et al. | |
| 5,135,759 A | 8/1992 | Johnson | |
| 5,406,421 A | 4/1995 | Kashima et al. | |
| 5,658,892 A | 8/1997 | Flotte et al. | |
| 5,739,902 A | 4/1998 | Gjelsnes et al. | |
| 6,010,647 A | 1/2000 | Nomura et al. | |

(Continued)

FOREIGN PATENT DOCUMENTS

DE 1815352 A1 1/1971

(Continued)

OTHER PUBLICATIONS

Garner et al.,Quantification of the X- and Y-Chromosome-Bearing Spermatozoa of Domestic Animals by Flow Cytometry, Biology of Reproduction, vol. 28, No. 2, Mar. 1, 1983, pp. 312-321.*

(Continued)

*Primary Examiner* — F. L. Evans
(74) *Attorney, Agent, or Firm* — Marshall, Gerstein & Borun LLP

(57) ABSTRACT

A method, apparatus, and system for a sorting flow cytometer include an objective lens having an optical axis coaxially aligned with the flow path at the focal point. A controllable energy source selectively alters an analyte according to a determination of whether the analyte is in a desired subpopulation. In various embodiments, one or both of the emission from the controllable energy source and/or the emission from an illumination energy source passes through the objective lens. In some embodiments in which the emission from the controllable energy source passes through the objective lens, the objective lens may focus the emission from the controllable energy source at a different point than the focal point of a signal detected from the analyte and, in particular, at a point closer to the objective lens.

43 Claims, 14 Drawing Sheets

U.S. PATENT DOCUMENTS

| | | | |
|---|---|---|---|
| 6,143,535 | A | 11/2000 | Palsson |
| 6,534,308 | B1 | 3/2003 | Palsson et al. |
| 6,594,009 | B2 | 7/2003 | Saccomanno |
| 7,106,528 | B2 | 9/2006 | Ohmori et al. |
| 7,118,676 | B2 | 10/2006 | Mueth et al. |
| 7,193,775 | B2 | 3/2007 | Olszak et al. |
| 7,355,696 | B2 | 4/2008 | Mueth et al. |
| 7,586,604 | B2 | 9/2009 | Sharpe et al. |
| 2005/0112541 | A1 | 5/2005 | Durack et al. |
| 2005/0194546 | A1 | 9/2005 | Saccomanno |
| 2006/0263829 | A1 | 11/2006 | Evans et al. |
| 2007/0117086 | A1 | 5/2007 | Evans et al. |
| 2008/0144037 | A1 | 6/2008 | Mueth et al. |

FOREIGN PATENT DOCUMENTS

| | | | |
|---|---|---|---|
| WO | WO-94/22001 | A1 | 9/1994 |
| WO | WO-98/34094 | A1 | 8/1998 |
| WO | WO-99/05504 | A2 | 2/1999 |
| WO | WO-2004/01704 | A2 | 2/2004 |
| WO | WO-2004/088283 | A2 | 10/2004 |
| WO | WO-2004/104178 | A2 | 12/2004 |
| WO | WO-2005/075629 | A1 | 8/2005 |
| WO | WO-2008/128630 | A1 | 10/2008 |
| WO | WO-2009/014643 | A1 | 1/2009 |
| WO | WO-2009/151624 | A1 | 12/2009 |

OTHER PUBLICATIONS

International Search Report and Written Opinion for Application No. PCT/IB2009/006480, dated Feb. 16, 2010.

Takahahi, et al., "Further advancement of wide-angle EUSO telescope with holographic and Fresnel lenses," 29th International Cosmic Ray Conference Pune 8, pp. 355-358 (2005).

Garner, et al., "Quantification of the X- and Y-Chromosome-Bearing Spermatozoa of Domestic Animals by Flow Cytometry," Biology of Reproduction 28, pp. 312-321 (1983).

Kawano, et al., "Ultrafast dynamics in a live cell irradiated by femtosecond laser pulses," Biophotonics 2007: Optics in Life Science, edited by Jurgen Popp, Gert von Bally, Proc. of SPIE-OSA Biomedical Optics, SPIE vol. 6633, pp. 66330J-1-66330J-9(2007).

Pitsillides, et al., "Selective Cell Targeting with Light-Absorbing Microparticles and Nanoparticles," Biophysical Journal, vol. 84, pp. 4023-4032 (2003).

Hung, et al., "Fluorinated Plastics, Amorphous," Concise Polymer Materials Encyclopedia, pp. 499-501 (1998).

Herweijer, et al., "High-Speed Photodamage Cell Selection Using Bromodeoxyuridine/Hoechst 33342 Photosensitized Cell Killing," Cytometry vol. 9, pp. 143-149 (1988).

Pinkel, et al., "High Resolution DNA Content Measurements of Mammalian Sperm," Cytometry vol. 3, No. 1, pp. 1-9 (1982).

Kerker, et al., "An Optical Model for Fluorescence of Mammalian Sperm in Flow Cytometry," Cytometry vol. 1, No. 2, pp. 161-167 (1980).

Martin, et al., "Photodamage, a Basis for Super High Speed Cell Selection," Cytometry vol. 2, p. 2 (Abstract) (1981).

Severin, et al., "A New Flow Chamber and Processing Electronics for Combined Laser and Mercury Arc Illumination in an Impulscytophotometer Flow Cytometer," Cytometry, vol. 3, No. 4, pp. 308-310 (1983).

Bakker Schut, et al., "A New Principle of Cell Sorting by Using Selective Electroporation in a Modified Flow Cytometer," Cytometry, vol. 11, pp. 659-666 (1990).

Keij, et al., "Coincidence in High-Speed Flow Cytometry: Models and Measurements," Cytometry, vol. 12, pp. 398-404 (1991).

Keij, et al., "High-Speed Photodamage Cell Selection Using a Frequency-Doubled Argon Ion Laser," Cytometry, vol. 19, pp. 209-216 (1995).

Evenson, et al., "Comparative Sperm Chromatin Structure Assay Measurements on Epiillumination and Orthogonal Axes Flow Cytometers," Cytometry, vol. 19, pp. 295-303 (1995).

Sharpe, et al., "Radially Symmetric Excitation and Collection Optics for Flow Cytometric Sorting of Aspherical Cells," Cytometry, vol. 29, pp. 363-370 (1997).

Koller, et al., "High-Throughput Laser-Mediated in Situ Cell Purification with High Purity and Yield," Cytometry Part A, vol. 61A, pp. 153-161 (2004).

Cytop®, "Amorphous Fluorocarbon Polymer," (undated) Available at http://www.belexinternational.com/Cytopflyer.pdf.

Gledhill, "Cytometry of Mammalian Sperm," Gamete Research, vol. 12, pp. 423-438 (1985).

Egner, et al., "Aberrations in Confocal and Multi-Photon Fluorescence Microscopy Induced by Refractive Index Mismatch," Handbook of Biological Confocal Microscopy, third edition, (2006).

Van Dilla, et al., "Measurement of Mammalian Sperm Deoxyribonucleic Acid by Flow Cytometry," The Journal of Histochemistry and Cytochemistry, vol. 25, No. 7, pp. 763-773 (1977).

Otto, et al., "Flow Cytometry of Human Spermatozoa," Histochemistry 62, pp. 249-254 (1979).

König, et al., "Effects of ultraviolet exposure and near infrared laser tweezers on human spermatozoa," Human Reproduction vol. 11 No. 10, pp. 2162-2164 (1996).

Phywe, Impulscytophotometrie ICP11 Book, pp. 1-24 (1973).

Phywe, Impulscytophotometrie ICP 22 Datasheet (1976).

Takizawa, et al., "Advancement of the wide-angle JEM-EUSO optical system with holographic and Fresnel lenses," 30th International Cosmic Ray Conference ICRC 2007 Proceedings—Pre-Conference Edition (2007).

Zohdy, et al., "Acoustic Estimation of Thermal Distribution in the Vicinity of Femtosecond Laser-Induced Optical Breakdown," IEEE Transactions on Biomedical Engineering, vol. 53, No. 11, pp. 2347-2355 (2006).

Zohdy, et al., "Optical and Acoustic Detection of Laser-Generated Microbubbles in Single Cells," IEEE Transactions on Ultrasonics, Ferroelectrics, and Frequency Control, vol. 52, No. 1, pp. 117-125 (2006).

Thøgersen, et al., "Reproductive death of cancer cells induced by femtosecond laser pulses," Int. J. Radiat. Biol., vol. 83, No. 5, pp. 289-299 (2007).

Pinkel, et al., "Flow Cytometric Determination of the Proportions of X-andY-Chromosome-Bearing Sperm in Samples of Purportedly Separated Bull Sperm," Journal of Animal Science 60:1303-1307, (1985).

Roegener, et al., "Pump-probe detection of laser-induced microbubble formation in retinal pigment epithelium cells," Journal of Biomedical Optics, vol. 9, No. 2, pp. 367-371 (2004).

Lee, et al., "Optical detection of intracellular cavitation during selective laser targeting of the retinal pigment epithelium: dependence of cell death mechanism on pulse duration," Journal of Biomedical Optics, vol. 12, No. 6, pp. 064034-1-064034-14 (2007).

Fulwyler, "Hydrodynamic Orientation of Cells," The Journal of Histochemistry and Cytochemistry, vol. 25, No. 7, pp. 781-783 (1977).

Steinkamp, et al., "Dual-Laser Flow Cytometry of Single Mammalian Cells," The Journal of Histochemistry and Cytochemistry, vol. 27, No. 1, pp. 273-276 (1979).

Balak, et al., "Regenerated Hair Cells Can Originate from Supporting Cell Progeny: Evidence from Phototoxicity and Laser Ablation Experiments in the Lateral Line System," The Journal of Neuroscience, vol. 10, No. 8, pp. 2502-2512 (1990).

Gledhill, et al., "Flow Microfluorometric Analysis of Sperm DNA Content: Effect of Cell Shape on the Fluorescence Distribution," J. Cell. Physiol., vol. 87, pp. 367-376 (1975).

Vogel, et al., "Femtosecond Plasma-Mediated Nanosurgery of Cells and Tissues," Laser Ablation and its Applications, pp. 231-280 (2007).

Lapotko, et al., "Spectral Evaluation of Laser-Induced Cell Damage with Photothermal Microscopy," Lasers in Surgery and Medicine, vol. 36, pp. 22-30 (2005).

Keij, et al., "High-Speed Photodamage Cell Sorting: An Evaluation of the ZAPPER Prototype," Methods in Cell Biology, vol. 42, pp. 371-386 (1994).

Oldfield, "Light Microscopy: An Illustrated Guide," A Mosby Ltd., p. 160 (1993).

Tanabe, et al., "Multiphoton excitation-evoked chromophore-assisted laser inactivation using green fluorescent protein," Natural Methods, vol. 2, No. 7, pp. 503-505 (2005).

Crosland-Taylor, "A Device for Counting Small Particles suspended in a Fluid through a Tube," Nature, vol. 171, pp. 37-38 (1953).

Meistrich, et al., "Resolution of X and Y spermatids by pulse cytophotometry," Nature, vol. 274, pp. 290-291 (1978).

Tirlapur, et al., "Targeted transfection by femtosecond laser," Nature, vol. 418, pp. 290-291 (2002).

Brenner, et al., "Water Immersion Objectives," Nikon Instruments, Inc., Available at http://www.microscopyu.com/articles/optics/waterimmersionobjectives.html (date unknown, accessed Apr. 23, 2009).

White, et al., "Manufacture of Perfluorinated Plastic Optical Fibers," Optical Fiber Communication Conference, Available at http://ieeexplore.ieee.org/xpl/freeabs_all.jsp?arnunnber=1362102 (2004).

He, et al., "Targeted photoporation and transfection in human HepG2 cells by a fiber femtosecond laser at 1554 nm," Optics Letters, vol. 33, No. 24, pp. 2961-2963 (2008).

Keu, et al., "Reduced Photoinactivation of 10-Dodecyl Acridine Orange-Sensitized Yeast Cells at High Fluence Rates: Measurements and Computer Simulations," Photochemistry and Photobiology, vol. 60, No. 5, pp. 503-509, (1994).

Mir, et al., "Two-photon absorption of copper tetrasulfophthalocyanine induces phototoxicity towards Jurkat cells in vitro," Photochemical and Photobiological Sciences, vol. 5, pp. 1024-1030 (2006).

Sarkar, et al., "Constancy in Human Sperm DNA Content," Proceedings of the National Academy of Sciences, vol. 71, No. 9, pp. 2512-3516 (1974).

M. Li, "POFnet, Plastic Optical Fiber (POF) The Last Few Hundred Meters," Hakko Optical, (2007).

H.M. Shapiro, "Practical Flow Cytometry," John Wiley & Sons, Inc., Available at http://dx.doi.org/10.1002/0471722731.ch8, pp. 266-267 (2003).

Mullaney, et al., "Cell Sizing: A Light Scattering Photometer for Rapid Volume Determination," The Review of Scientific Instruments, vol. 40, No. 8, pp. 1029-1032 (1969).

Merrill, et al. "An Improved Cell Volume Analyzer," The Review of Scientific Instruments, vol. 42, No. 8, pp. 1157-1163 (1971).

Steinkamp, et al., "A New Multiparameter Separator for Microscopic Particles and Biological Cells," Rev. Sci. Instrum., vol. 44, No. 9, pp. 1301-1310 (1973).

Kashima, "Development of Laser Scanning Microscopy Using a Near Ultraviolet Laser," Scanning, vol. 17, pp. 66-69 (1995).

Fulwyler, "Electronic Separation of Biological Cells by Volume," Science, New Series, vol. 150, No. 3698, pp. 910-911 (1965).

Dilla, et al., "Cell Microfluorometry: A Method for Rapid Fluorescence Measurement," Science, New Series, vol. 163, No. 3872, pp. 1213-1214 (1969).

Pinkel, et al., "Sex Preselection in Mammals? Separation of Sperm Bearing Y and "O" Chromosomes in the Vole Microtus oregoni," Science, vol. 218, pp. 904-906 (1982).

Kang, et al., "Cancer-Cell Targeting and Photoacoustic Therapy Using Carbon Nanotubes as "Bomb" Agents," Carbon Nanobtubes for Photoacoustic Cancer Therapy, Small 2009, Available at http://www.smalljournal.com (2009).

Abramowitz, et al., "Molecular Expressions Optical Microscopy Primer Specialized Techniques," The Florida State University, Downloaded from http://micro.magnet.fsu.edu/primer/techiques/oblique/obliqueintro.html on Jun. 8, 2009 (Last modified 2003).

Abramowitz, et al., "Molecular Expressions Optical Microscopy Primer Anatomy of the Microscope," The Florida State University, Downloaded from http://micro.magnet.fsu.edu/primer/anatomy/kohler.html on Jun. 8, 2009 (Last modified 2003).

Asbury, et al., "Polarization of Scatter and Fluorescence Signals in Flow Cytometry," Cytometry vol. 40 pp. 88-101 (2000).

Fouque, et al., "Multiple wavelength fluorescence enhancement on glass substrates for biochip and cell analyses," Biosensors an Bioelectronics vol. 20 pp. 2335-2340 (2005).

Kummrow, et al., "Microfluidic structures for flow cytometric analysis of hydrodynamically focussed blood cells fabricated by ultraprecision micromachining," The Royal Society of Chemistry vol. 9 pp. 972-981(1999).

Seitzinger, et al., "Ray tracing analysis of the image quality of a high collection efficiency mirror system," Applied Optics vol. 29, No. 28 pp. 4255-4258 (1990).

* cited by examiner

METHOD AND APPARATUS FOR SORTING CELLS

RELATED APPLICATIONS

This application claims priority to U.S. Provisional Application No. 61/077,083, filed Jun. 30, 2008, the entire disclosure of which is incorporated herein by reference. This application is related to concurrently-filed U.S. patent application Ser. No. 12/495,437, the entire disclosure of which is also incorporated herein by reference.

FIELD OF THE INVENTION

The present invention relates, in general, to methods and apparatus for sorting cells and, in particular, to methods and apparatus for using a controlled energy source to modify a population of cells of interest by selectively removing, enriching, or altering cells, viruses, or particles from the population.

BACKGROUND

Flow cytometric sorting permits the selection, enrichment, apportionment, or division of populations of cells, viruses, bodies or particles of interest (hereinafter referred to as cells). The selection criteria include measurable properties of individual cells that can be detected from outside the cell, with or without the aid of chemical reagents or of complexes or bodies that are, or that may be caused to be, associated with the cell. For instance, properties of cells may be measured or approximated by detecting and/or quantifying the association of the cells with one or more labels, such as molecules, complexes, or bodies that fluoresce or have been modified to be rendered fluorescent. Such fluorescent molecules, complexes, and/or bodies may differentially associate with cells on the basis of qualitative or quantitative properties of the cells, including their composition with respect to proteins, lipids, phosphoproteins, glycoproteins, phospholipids, glycolipids, nucleic acids (including the quantity, sequence, or organization of nucleic acids), carbohydrates, salts/ions, and any other molecules in, on, or associated with the cells. Further, such fluorescent molecules, complexes, and/or bodies may differentially associate with cells based on physical or physiological characteristics of the cells, examples of which include but are not limited to membrane permeability, membrane composition, membrane fluidity, chemical or membrane potential, viability, chemical gradients, motility, reduction or oxidation potential or state, and other parameters or properties.

Other measurable properties of cells, whether labeled or unlabelled, modified or unmodified, that may provide a basis for cell selection may include but are not limited to:

properties of light interacting with the cells, such as fluorescence, absorbance, reflectance, scatter, polarization, or other properties;

electrical properties of the cells or of the effect of the cells on their environment, including conductance, inductance, resistance, membrane potential or voltage, or other properties;

magnetic or electromagnetic properties of cells, including magnetism, paramagnetism, magnetic resonance, and/or interaction of the cells with electromagnetic energy;

the appearance, image, or morphological properties of the cells; and the makeup of the cells with respect to any substance or parameter, measured directly or indirectly in any way.

Furthermore, the measurement of such parameters, directly or indirectly, singularly or in combination, may reflect simple or complex properties of interest of the cells.

One example of such a property is the sex chromosome included in the diploid, haploid, or gamete genome, which may be an X chromosome or a Y chromosome or combinations of both depending on the cell type and the organism. The determination of sex chromosome content may be inferred using direct or indirect measurements or determinations using one or more methods. Such methods include the measurement of the DNA content of the cells determined relatively or absolutely; the presence or absence of certain DNA sequences, or markers of the presence or absence of certain DNA sequences; the size of the cells or of portions or organelles of the cells; the presence, localization, or absence of proteins or other markers characteristic of the sex chromosome content of the cells, or combinations or patterns of expression of such markers; or any other measurement that reflects the sex chromosome composition of the cell. Many other such measurements may be made, or properties determined, to identify cells that are of interest in a particular instance, situation, system, disease, condition, process, or circumstance.

Such cytometric measurements permit quantitative and/or qualitative determinations about cells, populations of cells, organs, tissues, or organisms. Such determinations may be used in many ways including but not limited to diagnosis, biomedical research, engineering, epidemiology, medicine, agriculture, animal husbandry, livestock management, zoology, biopharmaceutical industry, and other fields. In addition to the ability to perform such measurements, current methods and instrumentation permit the separation of cells based on characteristics or parameters measured by cytometry as described above. Cells can be selected positively or negatively by the concentration, collection, or partitioning of cells of interest or by the removal of cells that are not desired or of interest in the preparation. Such selection can be controlled on the basis of any parameter, characteristic, or combination of parameters or characteristics that can be determined as described above.

Cells identified by methods including or related to those described above can be separated, partitioned, concentrated, depleted, or collected into any arbitrary number of groups. One common separation method (depicted in FIG. 1A) uses electrostatic forces to divert an electrically or electrostatically charged stream, droplet, or droplets containing a cell or cells having desired or undesired properties. The diverted cells are collected or discarded as appropriate to the particular application, as illustrated in FIG. 1A. Other separation methods include the use of fluidic devices including valves to divert cells in a fluid stream to alternate pathways, channels, tubes, or elements for subsequent collection or disposal, as illustrated in FIG. 1B.

There exist a number of methods and systems for performing flow cytometric sorting of cells. Among these are methods and systems designed specifically to perform flow cytometric sorting of mammalian sperm cells and, in particular, to sort the sperm cells into populations of sperm cells bearing X chromosomes and/or populations of sperm cells bearing Y chromosomes, with the purpose of increasing the probability that fertilization of an egg with the sorted sperm will result in offspring with a desired gender. For example, a dairy farmer may desire to sort the sperm of a bull so that bovine embryos may be produced, by artificial insemination, in vitro fertilization, or other means, with sperm having an X chromosome to produce additional female bovine offspring.

Flow cytometric sorting methods present a number of challenges, particularly with respect to sorting mammalian sperm cells for later use in producing offspring. Importantly, methods used to label and/or to differentiate between the cells and/or methods used to sort the cells must not adversely affect the viability of the cells. Often, one or more goals of the methods and/or systems involved (e.g., faster sorting, improved accuracy, etc.) conflict with other goals of the methods and/or systems. Various factors must be balanced and considered, including the temperatures, temperature changes, pressures and/or pressure changes to which the cells are subjected, the fluidic environments to which the cells are exposed, the forces applied to the cells, and the lifespan of the cell. For example, the rate at which a fluorescent molecule (e.g., a fluorochrome) enters a cell to bind to DNA within the nucleus of the cell (i.e., the rate at which cells may be stained), may increase as temperature increases. Thus, the throughput of a system (at least the throughput of the staining process) may increase with an increase in the temperature of the cells' environment. However, increased temperature may prove detrimental to the viability of the cells and/or the length of time that the cells remain viable. By contrast, maintaining the cells at the optimal temperature for viability may increase the time required for staining (and measuring and sorting) the cells, such that the process takes longer than is practical or such that the cells are not viable after the time required to complete the process.

Another challenge associated with sorting cells relates to the physical and optical properties of the cells. In particular, flattened or otherwise asymmetrical cells, such as mammalian red blood cells or sperm cells, exhibit anisotropic emission of energy (e.g., light). The complex geometries of a cell's interior and/or the complex geometries of the cell's boundaries act to refract and/or reflect light in ways that are highly dependent on the orientation of the cell with respect to any illumination sources and/or detectors used to differentiate between cells. For example, flow cytometry sorting of mammalian sperm cells into populations having X or Y chromosomes usually involves staining the cells with a fluorescent molecule that binds to DNA within the cells. The variation in DNA content between the X and Y chromosomes of most mammalian species (Y chromosomes generally containing less DNA than X chromosomes) results in relatively greater fluorescence from cells containing X chromosomes. However, the difference in DNA content of X and Y chromosomes is typically on the order of only a few percent and, often, cell geometry and/or orientation can affect the detected fluorescence by a percentage that far exceeds the percentage difference in DNA content between the X and Y chromosomes. Additionally, such analysis requires that cells pass through the detection region singly, such that a detector does not interpret fluorescence from two cells as fluorescence from a single cell.

Flow cytometry sorting systems frequently employ a core-in-sheath fluidic mechanism to carry the cells through the detection region. As depicted in FIG. 1C, a relatively slow moving stream 50 of an aqueous suspension of cells 52 is injected into a relatively faster moving flow 54 of sheath fluid. This arrangement focuses the cells 52 into a stream 56, referred to as the core stream. With appropriate selection of the pressures and consequent velocities of the core suspension and sheath fluid, the core stream is narrowed by hydrodynamic forces exerted by the sheath flow, and the cells in the core stream are distributed longitudinally such that they are carried one by one in the flow. The forces that elongate and narrow the core stream have the additional benefit of orienting the cells 52 such that a lengthwise axis 58 of the cell 52 is parallel to the direction of flow of the single file stream 56. However, the orientation of the cells about the lengthwise axis 58 remains more or less random. Thus, as each cell 52 passes through the detection area, light incident upon the cell, light emitted from the cell (e.g., fluorescent light), and light reflected off of the cell, remains dependent on the orientation of the cell 52. This is especially true of many types of mammalian sperm cells.

There are a number of solutions to the problem of sperm cell orientation with respect to illumination and detection of cells within flow cytometry systems. For example, FIG. 1D illustrates one solution, which solution employs a cut, beveled tip 60 on a tube 62 injecting a sample stream 64 into a sheath flow 66. The flattened, beveled tip 60 helps to orient the cells about their lengthwise axes 58 within the sheath flow 66 such that the flat faces of the cells tend to align in a consistent direction. Another solution (which may be combined with the beveled tip solution) employs two detectors 68 and 70 orthogonal to each other (a 0-degree detector 68 and a 90-degree detector 70) which are used in combination to estimate the orientation of each cell 52 as it passes through a detection area 72 and to measure the fluorescence of those cells that are found to be appropriately oriented such that precise quantization of the fluorescent signal is possible. The solutions employing hydrodynamic orientation of cells around the lengthwise axis generally yield populations in which the desired alignment for fluorescence measurement is achieved for about 70% or less of the cells in the sample flow, which decreases the throughput of the instrument and results in the discarding of improperly oriented cells.

Still another solution to the problems associated with cell geometry and orientation utilizes optical detection along the same axis as the core-in-sheath flow that carries the cells. In one such solution, epi-illumination optics are used to illuminate the cell and detect light emitted by the cell. As depicted in FIG. 1E, a sample stream 74 carried by a sheath flow 76 travels directly towards a microscope objective lens 78, eliminating the dependence on the orientation of the cell (e.g., a sperm cell 80) about a lengthwise axis 82 of the cell 80. However, the trajectory of the cell 80 towards the objective lens 78 requires that the cell 80 change trajectory immediately after passing through a detection area 82 (i.e., the focal point 84 of the objective lens 78). The system accomplishes this trajectory change by using a transverse flow 86 of fluid. Uncertainty in the position of individual cells may be introduced after the analysis by the convergence 88 of the transverse fluid flow 86 and the sheath flow 76 and fluid stream 74. Such position uncertainty may render the system inoperable to perform cell sorting because the location of the cell 80 within the converged flow may become unpredictable immediately after the cell passes through the detection area 82.

Yet another solution, illustrated in FIG. 1F, utilizes one or more parabolic reflectors 102 to illuminate cells uniformly and/or to collect light radially from the cells. The system utilizes a nozzle 104 to emit a stream/jet 106 of liquid containing individual cells 92. The stream 106 moves through a detection region 94 and through a hole 96 in the parabolic reflector 102. At some point after passing through the detection region, the stream 106 is broken into droplets 90 which may be electrically charged. Thereafter, each of the droplets 90 may be sorted by, for example, deflecting the charged droplet 90 and electrically charged deflector plates 98 to deflect the droplets into one or more receptacles 100. Problematically, this "jet-in-air" configuration subjects the stream 106 (and the cells 92 contained within the stream 106) to a drop in pressure as the stream 106 exits the nozzle 104. Sudden changes in pressure (and the increased pressures within the nozzle itself), can adversely affect the viability of the cell 92 as can the subsequent impact of the cell 92 into the receptacle 100. Thus, the pressure and speed of the stream 106 exiting the nozzle 104 must remain below any threshold that could damage the cells 92, which decreases the throughput of the system. Additionally, the movement of the droplets 90 through the atmosphere may require environmental constraints including cleanliness of the room air (e.g., a "clean room") and temperature-control.

Thus, even with the relatively advanced state of flow cytometry, there exists an ongoing need in the art to provide more efficient, more sensitive, and more precise methods of and devices for cell separation and/or identification.

SUMMARY

A method and apparatus is described for detecting, selectively altering by functional and/or physical modification, and collecting desired or undesired cells in a population using flow cytometry. The method does not rely on parabolic reflectors or orthogonal detection to detect and categorize cells, as is the case for common existing cytometric sorting methods and apparatus. Instead, the method employs an objective lens having an optical axis coaxial with the flow of the sample through a detection area. The method may or may not rely on the diversion or breakup of the flow stream of cells or the assortment of cells to different receiving vessels or pathways, as is also the case for common existing cytometric sorting methods and apparatus.

The method contemplates the use of a controllable energy source, such as, but not limited to, an electromagnetic radiation source such as a laser, to irradiate desired or undesired cells in a population that have been identified using cytometric detection techniques. The controllable energy source is selectively directed to cells of interest based on their measured properties or characteristics, after their analysis in the cytometer, in certain aspect within one second of their analysis while the cells remain in the fluidic flow of the device. Such cells may be functionally or physically altered by the imparted energy. Depending on the particular use and the particular embodiment of the methods or apparatus, the resulting cell population may be functionally or physically depleted of undesired cells, or may be modified in such a way as to permit the subsequent enrichment of desired cells or the removal of undesired cells. The described methods and apparatus are broadly useful in applications where the enrichment or depletion of cells is required. In some embodiments, the method and/or apparatus alters liquid containing desired or undesired cells in a population that have been identified using cytometric detection techniques, and may not alter the cells directly. In such embodiments, the method and/or apparatus may rely on the diversion or breakup of the flow stream of cells or the assortment of cells to different receiving vessels or pathways.

One aspect of the described methods and apparatus includes the use thereof for enrichment, selection, functional alteration, or depletion of sperm cells in a population on the basis of the sex chromosome, X or Y, contained in the cells. The methods and apparatus include the use of alternate designs for the fluidics and optical systems of a cytometer, including in one aspect, an apparatus where optical measurement components and/or a cell-altering energy source are/is oriented orthogonal to the fluidic stream, and in another aspect, an apparatus where some such components may also or alternatively be oriented in the same axis as the fluidic stream and/or at oblique angles to it.

The flow cytometric methods and apparatus provide a novel method and apparatus permitting positive or negative selection of cells by observing the cells and accurately classifying each cell independently of the cell's orientation about its longest axis, and subsequently using the classification to determine whether to modify, derivatize, damage, kill, or fragment the cell in the course of the cytometry procedure. The presently described methods and apparatus incorporate the application of forces, energy, or irradiation to desired or undesired cells coincident with or following within one second of the cytometric measurement to effect changes in those cells that alter them physically or functionally. Such altered cells, or their debris or derivatives, are in one aspect retained in the resulting preparation or in other aspects are enriched or removed, depending on the requirements of the particular use or application.

An embodiment is described that permits the functional and/or physical separation of spermatozoa bearing X chromosomes from spermatozoa bearing Y chromosomes and/or of spermatozoa bearing Y chromosomes from spermatozoa bearing X chromosomes. In this embodiment, the relative DNA content of individual spermatozoa in a population of spermatozoa is measured indirectly, utilizing a well known property of DNA-associating chemicals such as, but not limited to, bisbenzimide, SYBR dyes, such as SYBR-14, Hoechst 33342, Hoechst 33258, ethidium bromide, acridine orange, DAPI, chromomycin, mithramycin, olivomycin and other chemicals known in the art that exhibit enhanced fluorescence when associated with DNA. The measurement is accomplished by observing a cell as the cell moves within a stream flowing toward the observation point, preferably by an objective lens having an optical axis coaxial with the flow of the stream. Cells containing relatively more DNA (i.e., a higher DNA content) are presumed to contain the larger X chromosome, and cells containing relatively less DNA (i.e., a lower DNA content) are presumed to contain the smaller Y chromosome. In some embodiments of the method where cells having only one of the sex chromosomes are desired in the final preparation, the method utilizes a laser energy source directed to cells, in one aspect, coincident with or in another aspect, within one second or less of their analysis, where the laser energy source can be rapidly modulated to irradiate cells that contain the undesired sex chromosome and/or cells whose sex chromosome content is uncertain. In one aspect of this embodiment, the method utilizes a laser energy source that deposits energy of sufficient quality and/or quantity to modify, derivatize, disrupt, disable, and/or kill the undesired cells. Such changes in the selected cells involve, in one aspect, the fragmenting of the cells or, in an alternative aspect, are less disrupting, depending on the application. For example, in embodiments of the method where identified and/or isolated sperm are to be used for fertilization and/or reproduction, rendering undesired cells incapable of producing viable offspring, for instance by disruption of the sequence or structure of DNA molecules in the cells, or by decreasing their motility such that they are mostly infertile in use in artificial insemination, is in one aspect sufficient to produce the desired preparation. In other aspects, the undesired cells are rendered nonmotile, killed, modified, or inactivated in some other way to affect the reproductive capacity of the undesired cells. In an alternative aspect, undesired cells are modified or derivatized in a way that permits their subsequent removal or partial removal from the preparation of desired cells.

In another embodiment, the configuration of the cytometer employs one or more optical elements used, in one aspect, for the measurement of cellular properties and/or in another aspect, used in the delivery of energy to cells, wherein at least one optical element, preferably an optical axis of an objective lens, is oriented in the same axis as the flow of the cells undergoing analysis. Thus, in some embodiments, a method and apparatus is provided utilizing an optical element and, in particular, an objective lens positioned coaxial with the fluid flow, for the illumination, measurement, or delivery of energy to cells. In another embodiment, a method and apparatus is provided utilizing one or more additional optical elements, alone or in combination, positioned at 90 degrees to the fluid stream for measurements or for the delivery of energy to cells. In still another embodiment, a method and apparatus is provided utilizing one or more additional optical elements, alone or in combination, positioned non-coaxial to the fluid stream for measurements or for the delivery of energy to cells. In yet another embodiment, a method and apparatus is provided utilizing one or more additional optical elements, alone or in combination, positioned at an oblique angle to the fluid stream for measurements or for the delivery of energy to cells. As used herein, an "oblique angle" is an angle, such as an acute or obtuse angle, that is not a right angle or a multiple of a right angle.

Some embodiments provide a method for modifying a cell of interest in a population of cells comprising the step of contacting the cell of interest with a controllable energy source that modifies the cell of interest upon identification of a cell as a cell of interest in a population of cells, without separating the cell of interest from the population of cells upon modification by the energy source.

Some embodiments provide a method for identifying a subpopulation of cells of interest in a population of cells, comprising the step of contacting the population of cells with a controllable energy source that modifies cells of the subpopulation of cells of interest, wherein contacting takes place after a first analysis of the cells in a fluidic sample flow of a flow cytometer, and no longer than about one second after the first analysis, the cells remaining within the fluidic sample flow of the flow cytometer, wherein the first analysis identifies cells of the subpopulation of cells as cells of interest, as those cells of interest flow toward an interrogation area, and wherein the controllable energy source modifies the cells of interest in the sample flow through the flow cytometer.

In some embodiments, the first analysis comprises detecting the cells of interest as having a desired property selected from the group consisting of a desired: protein composition, DNA composition, cell surface marker, molecule size, light absorbance, light reflection, fluorescence, light scatter, polarization, electrical property, magnetic property, morphological property, membrane permeability, membrane fluidity and redox state.

In some embodiments, contacting the population of cells with the energy source occurs as the population of cells passes through a flow stream in a flow cytometer. In a related embodiment, the cell of interest is contacted with the energy source after, and within one second of, the identification of the cell as a cell of interest in the flow stream.

It is contemplated, in some embodiments, that the energy source is positioned co-axial to the flow stream. It is further contemplated that the energy source is positioned at a 90° angle to the flow stream, or positioned at an angle oblique to the flow stream. In another embodiment, the energy source is delivered to cells of interest via Köhler and/or epi-illumination optics. In another embodiment, the energy source is directed to a point in the flow of cells that is downstream of the position at which the cellular properties are measured. In another embodiment, the energy source is directed to a point in the flow of cells that is downstream of the position at which the cellular properties are measured and is after a diversion or turning of the flow stream from its original direction of flow.

In some embodiments, one or more analyses are accomplished by observing a cell as the cell moves within a stream flowing toward an observation point, preferably by an objective lens having an optical axis coaxial with the flow of the stream. After passing through the observation point, the stream changes directions in some embodiments, while the order and/or location of the cells within the stream remain determinable. In some embodiments, a controllable energy source may selectively alter one or more of the cells according to the one or more analyses. In some embodiments, the controllable energy source is positioned coaxial to the newly directed stream, while in other embodiments, the controllable energy source is positioned perpendicularly or at an oblique angle relative to the newly directed stream. In some embodiments, which may or may not include a controllable energy source, a nozzle may eject stream, forming droplets that may be sorted using known means (e.g., by using a controllable energy source to apply an electrostatic charge, controlling pressure in various fluid flow pathways, etc.).

In some related embodiments, the controllable energy source is directed to the location of the cell in a flow stream in a manner selected from the group consisting of continuous stream, pulsed stream, intermittent on/off cycles, periodic focus and defocus of the energy source and intermittent rapid diversion of the energy source to the stream.

In some embodiments, the controlled energy source is an electromagnetic source. In some embodiments, the energy source is a laser.

In some embodiments, the modification of the cells is selected from the group consisting of derivatizing, killing, damaging, disrupting and fragmenting the cells of interest.

In a further aspect, the cell of interest is identified as a cell of interest using a label detectable by electrical, magnetic, spectroscopic, photochemical, biochemical, immunochemical, fluorescent, or other chemical means. In some embodiments, the label is the addition of a photoactivatable chemical compound or label.

In a related embodiment, the cell of interest is identified as having a desired property selected from the group consisting of a desired: protein composition, protein content, DNA composition, DNA content, cell surface marker, molecule size, light absorbance, light reflection, fluorescence, light scatter, polarization, electrical property, magnetic property, morphological property, membrane permeability, membrane fluidity and redox state.

The described methods and apparatus contemplate that any energy source, detector, or focusing element used in the detection of properties of cells in the flow may be positioned co-axial to the flow stream. For example, in a flow cytometer comprising detectors and a controllable energy source, either the detectors or the controllable energy source, or both, are positioned co-axial to the flow stream. In a related embodiment, any detection apparatus and or optical elements used in the detection of properties of cells in the flow is positioned coaxial to the flow stream.

In a further embodiment, Köhler and/or epi-illumination optics are used for the delivery of light or energy used for the detection of desired properties. In a related embodiment, when the method uses a flow cytometer, the flow cytometer is an epi-illumination cytometer. It is further contemplated that an epi-illumination cytometer useful in the described method incorporates apparatus for the modification of cells of interest as further described herein.

When a flow cytometer is used in the described method, the flow cytometer is a flow cytometer having one or more sample streams and incorporates optics having an objective lens coaxial with the flow of the one or more sample streams for the delivery of light or energy used for the detection of desired properties, for the detection of desired properties of cells, and/or for the delivery of light or energy used for the modification of desired or undesired cells.

In a further embodiment, the energy source modifies the cell of interest having a desired property. In a related embodiment, the energy source modifies the cell of interest lacking a desired property.

In a still further embodiment, the cell of interest is a sperm cell selected from the group of X chromosome-bearing sperm and Y chromosome-bearing sperm. It is contemplated, in some embodiments, that the sperm cell is identified as a cell of interest based on a desired property of difference in DNA content between X chromosome-bearing sperm and Y chromosome-bearing sperm.

The described methods and apparatus further provide that the population of cells are collected in a collection chamber for further use. In some embodiments, the collection chamber contains cells of interest which have been modified by the controllable energy source and cells that have not been modified by the controllable energy source. In a related embodiment, after collection, the cells of interest may be used in subsequent processes or procedures. In a still further embodiment, it is contemplated that after collection, the cells of interest are discarded and the reminder of the population of cells are used in subsequent processes or procedures.

The described methods and apparatus also provide an apparatus for modifying a cell of interest in a population of cells comprising a controllable energy source that modifies the cell of interest upon identification of a cell as a cell of interest in a population of cells, without separating the cell of interest from the population of cells upon modification by the energy source.

In a related embodiment, the described methods and apparatus contemplate identifying a subpopulation of cells of interest from a population of cells, using a flow cytometer comprising a controllable energy source that modifies the subpopulation of cells of interest wherein the contacting takes place after a first analysis of the cells during sample flow through a sample tube of the flow cytometer, and usually within one second of the cell analysis, while the cells remain within the fluidic sample flow of the apparatus, wherein the first analysis identifies the cell as a cell of interest, and wherein the controllable energy source modifies the cell of interest during the sample flow through the flow cytometer.

In some embodiments, one or more steps of a described method are stored as machine-readable instructions on a tangible storage medium within a controller. A processor of the controller executes the instructions to monitor and/or control various aspects of a sorting flow cytometer. The instructions may be embody one or more routines adapted to various tasks within the cytometer.

In some additional embodiments, an optical cell, cuvette, window, flow tube, wall, boundary, or other part of a sorting flow cytometer is formed of a material having an index of refraction between 1.30 and 1.40, inclusive. In these and other embodiments, an analyte-bearing solution may be adjusted such that the refractive index of the solution is close to the refractive index of the optical cell, cuvette, window, flow tube, or other part of the sorting flow cytometer and, in particular, the refractive indices differ by 0.02 or less.

DETAILED DESCRIPTION

Figure 1A:
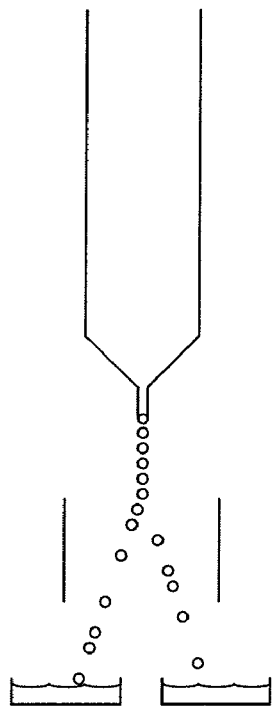
FIG. 1A illustrates a droplet sorting method employed in sorting flow cytometers.
Figure 1B:
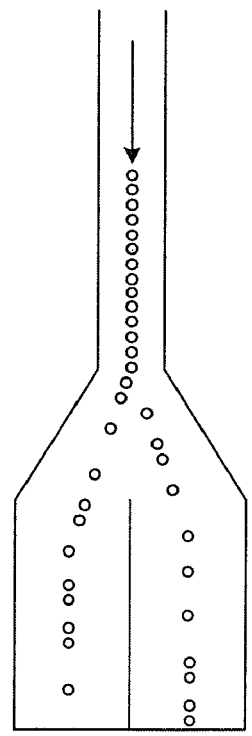
FIG. 1B illustrates a differential flow pressure method employed in sorting flow cytometers.
Figure 1C:
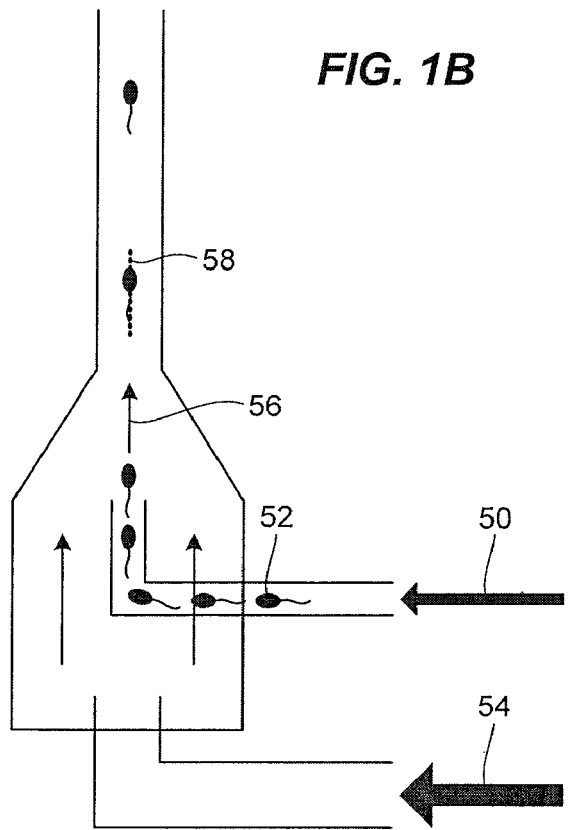
FIG. 1C depicts a sheath-and-stream mechanism employed in flow cytometry systems.
Figure 1D:
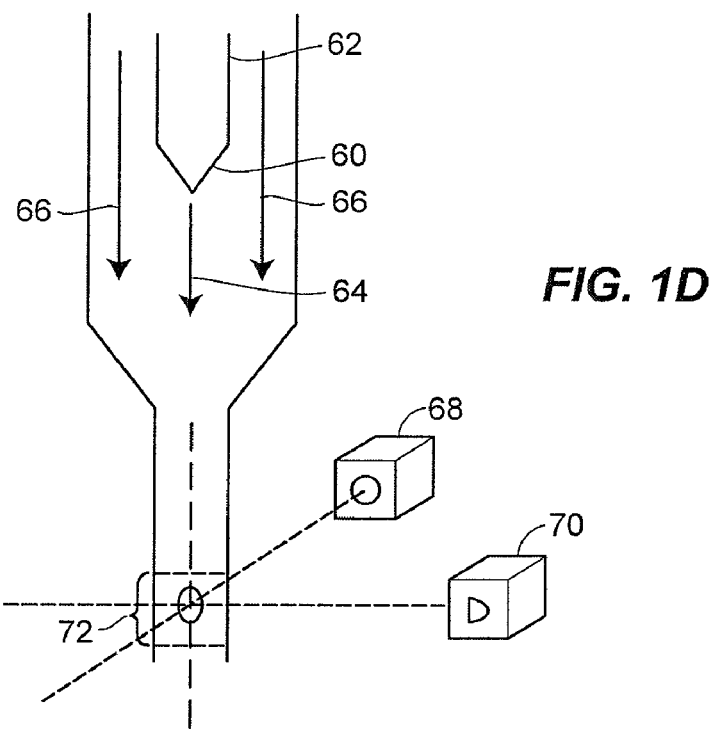
FIG. 1D depicts a sheath-and-stream mechanism that employs a beveled tip to orientate within the stream.
Figure 1E:
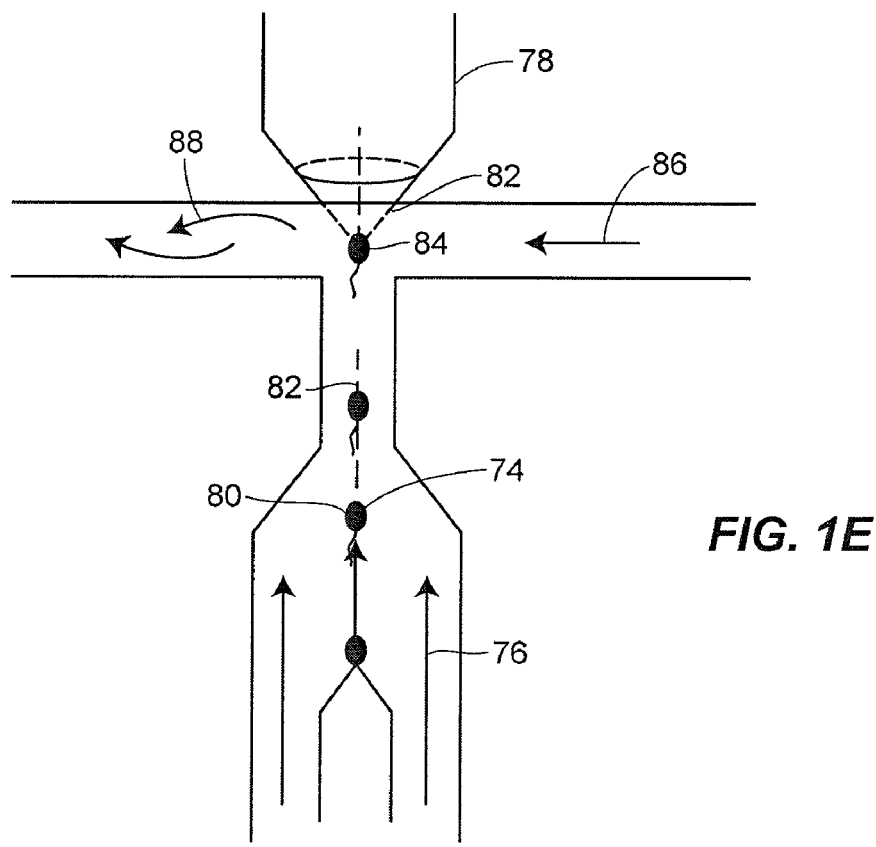
FIG. 1E depicts a flow cytometer detecting a cell using an objective lens oriented coaxially with the a flow stream.
Figure 1F:
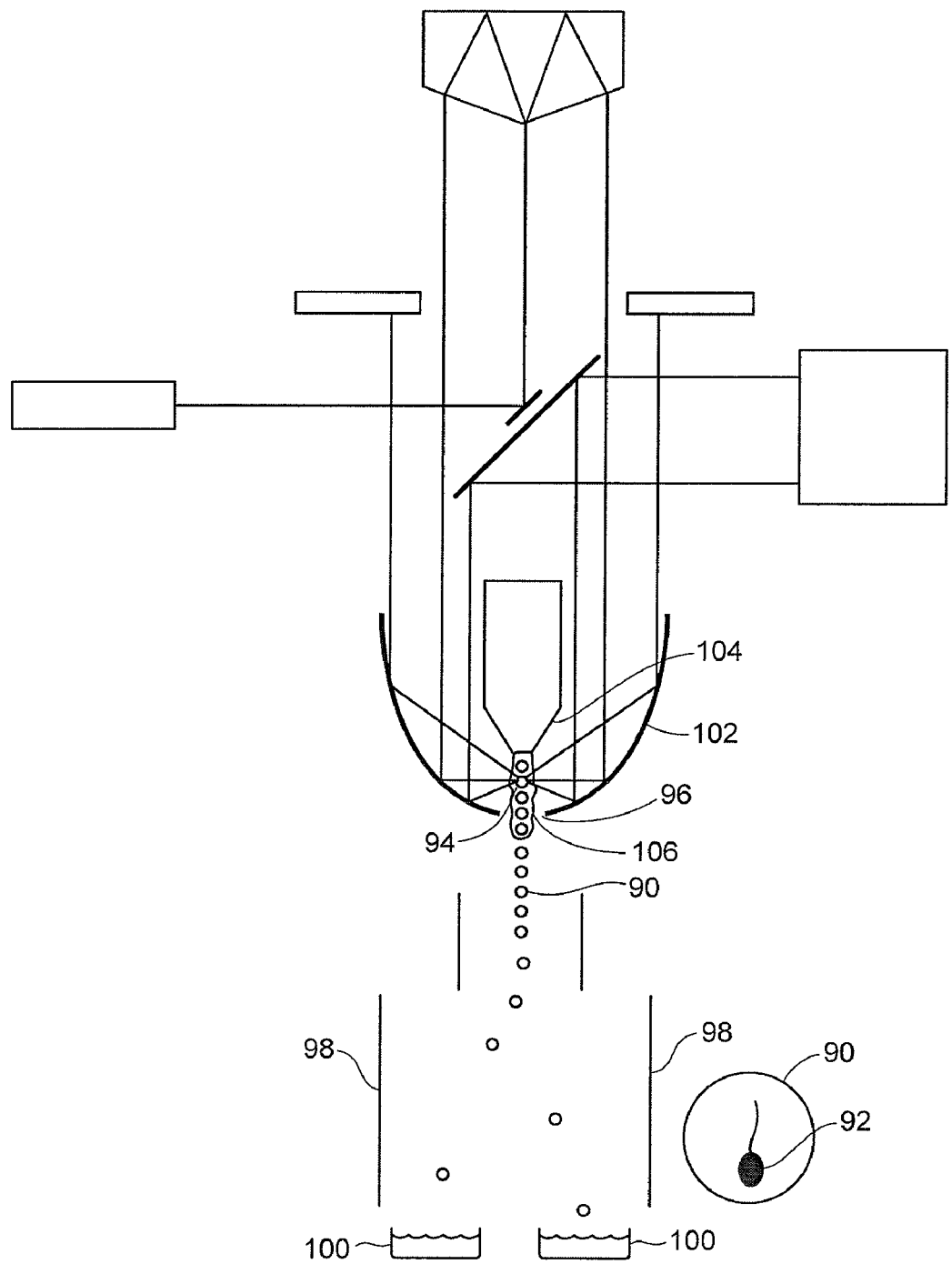
FIG. 1F illustrates a system using a parabolic reflector to illuminate cells uniformly and to collect light radially from the cells.

The present specification describes methods, systems, and apparatus for cell separation based on flow cytometry. Unless otherwise defined, all technical and scientific terms used herein have the same meaning as commonly understood by one of ordinary skill in the art to which this the claimed inventions belong.

It is noted here that, as used in this specification and the appended claims, the singular forms "a," "an," and "the" include plural reference unless the context clearly dictates otherwise.

As persons of ordinary skill in the art will readily appreciate, unless otherwise indicated as being important to the understanding of the described methods and apparatus, the included figures are not drawn to scale.

As used herein, the following terms have the meanings ascribed to them unless specified otherwise.

The term "cells" refers to the analyte in the described methods and apparatus, this matter including, but not limited to cells, viruses, bodies, or particles. The term "cells of interest" or "cell of interest" refers to a cell having a desired property which property can be detected during flow of the cell through the flow cytometric apparatus. A "desired property" refers to a certain characteristic that distinguishes the cell having the desired property from a cell not having said characteristics. Cells having a desired property are within a "desired sub-population" of cells. Exemplary measurable or detectable cell characteristics in a cell of interest include, but are not limited to, protein composition, protein content DNA composition, DNA content, cell surface markers, molecule size, light absorbance, light reflection, fluorescence, light scatter, polarization, electrical properties of the cells, magnetic properties, morphological properties, membrane permeability, membrane fluidity, and redox state. One of ordinary skill in the art will readily appreciate that a cytometer may measure or detect any of a number of alternative characteristics in a cell of interest, and that these alternative characteristics are readily amenable to exploitation in the described methods and apparatus. In one aspect, the methods or apparatus exploit a "desired property" of a cell of interest to identify cells having this property.

The term "first analysis" refers to an initial analysis of cells as the cells proceed through a flow cytometric apparatus, which can be a tube, a cuvette, a region, a cell, a chamber, etc., to determine if the cells are cells of interest. In an aspect of some embodiments, detectors in a flow cytometer execute the first analysis.

The term "second analysis" as used herein refers to characterization of the cell of interest after the first analysis through the flow tube to determine whether to alter the cell of interest using an energy source. In an aspect of some embodiments, the second analysis takes place after, usually less than one second after, the first analysis.

The terms "modify," "modification," "alter," and "alteration," as used herein, refer to using the energy source to induce changes to a cell. Modifications include, but are not limited to, direct effects on the cells, including but not limited to the modification of cellular components or chemicals including proteins, DNA, and substances involved in cellular metabolism; disruption, heating, cavitation, or explosions occurring in or near the cells; permeabilization or perforation of cells; and destruction, fragmentation, or morphological alteration of cells. In other aspects, modifications also or alternatively include indirect effects of the energy source, mediated by the energy source or by other factors, including chemical activation and/or deactivation, chemical crosslinking, or chemical derivitization of the cells or of one or more cellular components, the activation and/or deactivation of one or more chemical agents in or near the cells that cause the binding or association of such agents or their derivatives to the cell or its components, or the induction of altered functioning of the cells. In certain aspects, chemical agents, normally present within or otherwise applied to the cells, interact with the cells upon irradiation of the cells.

The described methods and apparatus permit identification of cells of interest by detecting the presence or absence of any number of characteristics (e.g., a desired property) or parameters that can be determined, estimated, or reflected in measurements compatible with flow cytometric techniques. Cytometric measurements used to define cells or cellular populations of interest include in various aspects those discussed herein and those otherwise known in the art, as well as novel measurement methods, mechanisms, and/or apparatus that may be introduced or made applicable to flow cytometric analysis. Cells subjected to cytometric analysis through practice of the presently described methods and apparatus, may be labeled or unlabelled, or otherwise modified or unmodified using techniques and reagents known in the art.

As used herein, the term "label" refers to a composition detectable by spectroscopic, photochemical, biochemical, immunochemical, or chemical means. For example, useful labels include fluorescent dyes, electron-dense reagents, enzymes, biotin-streptavidin, dioxigenin, haptens, proteins for which antisera or monoclonal antibodies are available, or nucleic acid specific dyes. Thus, in the presently described methods and apparatus, the makeup, properties, and/or characteristic of cells with respect to any substance or parameter, measured directly or indirectly in any way is the basis for the identification of cells and cell populations for selection or exclusion.

Examples of detectable makeup, properties, and/or characteristics of cells include, but are not limited to: measurements of properties of light interacting with the cells or emitted by the cells, such as absorbance, light scattering, luminescence, fluorescence, phosphorescence, polarization or depolarization of light, or other properties; properties of electricity including but not limited to inductance, capacitance, potential, current, or resistance of cells or of the surrounding medium; properties of electromagnetism including magnetism, paramagnetism, magnetic resonance, and/or interaction of the cell with or emission of electromagnetic forces and/or waves; imaging, image properties, morphological properties, or related properties derived from the collection and/or analysis of image or image-like properties of cells. In certain aspects, the measurement is an intrinsic quantity or quality of the cell, or in alternative aspects, the measurement is a value that indirectly reflects, represents, or approximates, a quantity or quality of the cell. In still other aspects, the measurement is both an intrinsic quantity or quality of the cell and an indirect reflection, representation, or approximation of a quantity or quality of the cell. By way of example and not limitation, a measure of fluorescence of a cell may reflect the intrinsic fluorescence of the cell or the measure of fluorescence of a cell may reflect the presence and/or quantity of a fluorochrome or fluorescent particle that binds to or associates with the cell and directly or indirectly reflects some property of the cell, or both.

In some aspects of the described methods and apparatus, a sorting cytometer employs a technique that results in the physical or spatial separation of cells and cell populations. In other aspects of the described methods and apparatus, a sorting cytometer utilizes a technique that physically and/or functionally modifies selected cells in populations to permit their functional and/or physical separation and/or differentiation, optionally for subsequent use. In some aspects of the described method and apparatus, a sorting cytometer does not rely on immediate separation of cells by position, location, vessel, or time, but instead provides cells are that inactivated, incapacitated, disrupted, disarticulated, fragmented, or otherwise altered (i.e., "modified") with respect to some desired property, that optionally allows separation or differentiation of subpopulations in the preparation. The nature of the modification depends, all or in part, on an intended application or use for identified cells, and thus, characteristics of the identified cells that are relevant in the application. For example and for purposes of explanation or clarification only, a malignant or otherwise immortal or rapidly growing cell might be considered functionally inactivated in the context of the preparation of normal somatic cells if the cell's capacity to reproduce is negatively affected or if the cell is killed. In another example, again for purposes of explanation or clarification only, where an application requires the removal from a population of a subpopulation of cells that produce an undesirable protein or other substance, a sorting cytometer may achieve this result by abrogating production of the substance in these cells, by killing the cells, and/or by modifying the cells to permit their physical removal from the population.

The methods and apparatus presently described utilize, in some embodiments, an energy source for modification of cells or for the induction or initiation of processes such as chemical activation that may modify cells. Modifications induced by the energy source include in various aspects, direct effects on the cells, including but not limited to the modification of cellular components or chemicals including proteins, DNA, and substances involved in cellular metabolism; disruption, heating, cavitation, or explosions occurring in or near the cells; permeabilization or perforation of cells; and destruction, fragmentation, or morphological alteration of cells, including cells, viruses, bodies or particles. In other embodiments, modifications also or alternatively include indirect effects of the energy source, mediated by the energy source or by other factors, including chemical activation and/or deactivation, chemical crosslinking, or chemical derivitization of the cells or of one or more cellular components, the activation and/or deactivation of one or more chemical agents in or near the cells that cause the binding or association of such agents or their derivatives to the cell or its components, or the induction of altered functioning of the cells. In certain embodiments, chemical agents that react upon irradiation with the cells are normally present in the cells or in the application, or they are added as part of the method.

In some embodiments, the described methods and apparatus incorporate the use of photoactivatable compounds that are induced to bind or associate with cells or cellular components upon irradiation with light of an appropriate intensity and energy. Such compounds in certain aspects induce sufficient crosslinking or denaturation of one or more cellular components that affect cellular processes or metabolism of cells of interest. Alternatively, such compounds in certain aspects induce sufficient crosslinking or denaturation of one or more cellular components that kill cells of interest. In another alternative, photoactivatable compounds used in the described methods and apparatus bind to selected cells and alter one or more properties of cells of interest in such a way as to render the cells of interest amenable to identification and/or enrichment and/or depletion in subsequent processes. Cells of interest that have been altered by chemical derivatization, such as the addition of a chemical substance, are in certain aspects removed, concentrated, or purified in a subsequent step by methods that utilize the properties or interactions of such a substance. For example, and for purposes of explanation and clarification only, cells of interest are, in one aspect, derivatized by the addition of a substance that is subsequently bound by an antibody that permits the capture or retention of the derivatized cell of interest by various means. Many such substances are contemplated, and in one aspect, such substances include a class of compounds containing or related to the 2,4-dinitrophenyl group (DNP), which in one aspect is recognized and specifically bound by antibodies recognizing DNP. Accordingly, photoactivatable derivatives of DNP or related compounds are used in one aspect to derivatize cells of interest in an application of this type. Alternatively, derivatized cells of interest are captured or removed using strategies that cause the derivatized cells of interest to bind preferentially to certain substrates. For example and for purposes of explanation and clarification only, cells of interest derivatized using compounds containing or related to biotin are in one aspect captured or retained on substrates, surfaces, substances, media, compounds, or particles that bind or have been modified to bind biotin, for instance by the presence of avidin, streptavidin, biotin-binding antibodies, or other biotin-binding molecules. In another alternative related to this aspect, photoactivatable derivatives of biotin or related compounds are used to derivatize cells of interest in such an application. Alternately in other aspects, cells of interest are altered by the addition or association of chemical substances or compounds before being subjected to selection and modification. In such a case, therefore, an embodiment of the methods and apparatus described herein utilizes alteration of the added substance on selected cells to permit the differentiation of such cells from others in the population. For instance, and for purposes of explanation and clarification only, in one aspect all cells in a population are derivatized by the addition of a photolabile chemical compound before analysis, and in one aspect, specific cells are targeted for modification using the energy source of the apparatus to modify the photolabile chemical compound on those cells.

In some embodiments of a cytometer (see FIG. 1), cells pass into an interrogation or analysis chamber, cuvette, stream, or other analysis position or region in the usual way, familiar in the art, for flow cytometric analysis and/or sorting. The cytometer identifies cells by their measured properties as described above, including but not limited to such properties as fluorescence and/or light scattering, as having a desired property or not having a desired property in the final preparation. A flow of fluid carries the cells through the region of the cytometer and, in one aspect, past one or more laser beams, detectors, and/or other apparatus that detect quantities and qualities of the cells. In one such aspect, the flow of fluid moves the cells toward an optical element having an axis generally coaxially aligned with the fluid flow. By way of example and not limitation, the optical element may include a lens, such as an objective lens, and/or may include one or more detectors, laser beams, and/or other energy sources. The light and/or energy passing between the cells and the detectors, laser beams, and or other energy sources may pass through the optical element (e.g., the objective lens) that is generally coaxially aligned with the flow the cells through the relevant portion of the cytometer. The position of each cell in the cytometer at any point in time is, in one aspect, determined directly or indirectly and/or estimated from the velocity of the cell or fluid passing through the relevant portion of the instrument. A cell that has passed some or all of the analysis position(s) in the region is, in one aspect, identified as having a desired property or not having a desired property in the final preparation. Such a determination is, in one aspect, made by a computer and/or analogue and/or digital electrical or electronic and/or software and/or computer hardware data analysis device or devices. Such a device compares individual or multiple properties, measurements, and/or characteristic of each cell to one or a set or group of properties, measurements, and/or characteristics defined by the operator of the apparatus. Alternatively, the properties to which the measured properties are to be compared are, in one aspect, determined automatically using algorithms or programs included in or with the cytometer.

The set of properties against which cells measured in the cytometer are compared in one aspect defines one or more subpopulations of cells of interest that have a desired property or do not have a desired property in the cell preparation. The determination of whether a cell that is passing through the analysis region of the instrument is a member of a particular subpopulation of cells of interest is, in one aspect, made rapidly such that the cell's status as having a desired property or not having a desired property in the cell preparation is determined at a time when the position of the cell in the flow system of the instrument is determined, in certain aspects, usually less than one second after entering the analysis region of the instrument. Once the determination has been made, cells in one aspect are acted upon by an energy or force that is selectively imparted to cells that satisfy or do not satisfy the selection criteria. The force or energy in various aspects inactivates, incapacitates, disrupts, disarticulates, fragments, or otherwise alters the cells of interest with respect to a desired property that is relevant to an optional subsequent application, or the force or energy in alternative aspects modifies, and/or derivatives, or causes the cells of interest to be derivatized in a way that permits subsequent separation or differentiation of one or more subpopulations of cells of interest in the preparation.

Such a force or energy, in various aspects, is imparted by one or more lasers or other light and/or electromagnetic sources directed to the location of cells in the flowing stream, in such a manner that the energy source can be rapidly diverted, defocused, or turned off to permit the passage of cells that are not selected for modification. For example, and for purposes of clarification and explanation only, a high energy and/or high intensity laser, capable of being rapidly pulsed or turned on and off, exposes selected cells to damaging radiation rendering them non-functional in the context of any desired use. In some aspects, the force or energy passes through an optical element generally coaxially aligned with the flow of cells as the cells pass through the relevant area of the cytometer. In any event, all cells, both those selected and acted upon by the modifying force or energy, and those not selected and not acted upon by the force or energy, continue to migrate with the cellular flow and exit the region of the apparatus in which the measurement of cellular properties and the modification of selected cells is performed. The effluent is collected and it contains modified and unmodified cells as well as, in certain aspects, fragments, or residues of cells, as well as fluid, solutions, and/or buffers used in the process. In various aspects, the effluent is used further in this form, or in other aspects it is concentrated, fractionated, or otherwise processed further to achieve desired properties and/or composition.

Figure 2:
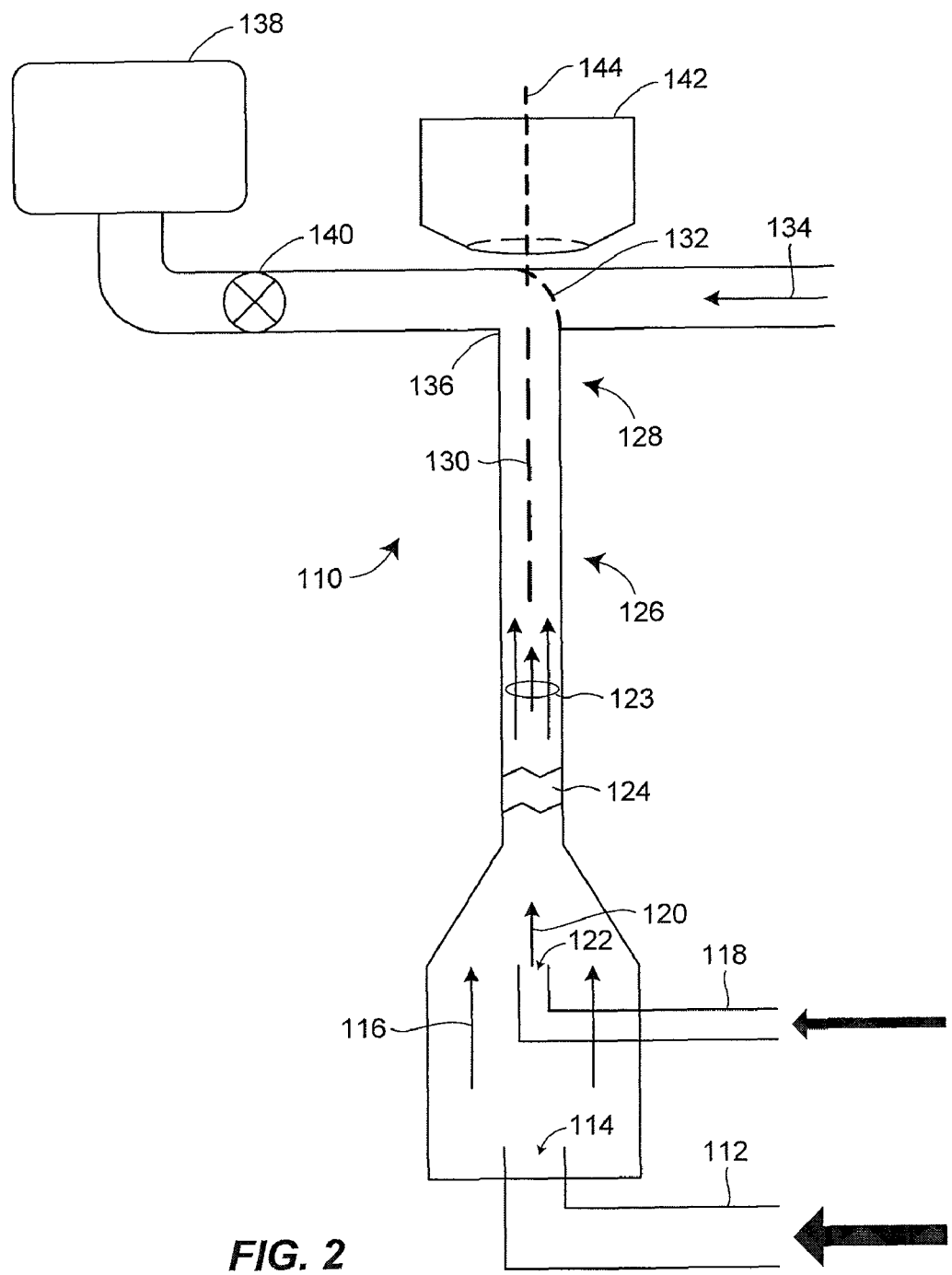
FIG. 2 depicts a contemplated embodiment of the flow path of a sorting flow cytometer.

FIGS. 2-5 depict various embodiments of a sorting flow cytometer according to the described methods and apparatus. FIG. 2 in particular depicts an embodiment of a basic flow path 110 of such a cytometer. A sheath fluid input tube 112 allows pressurized sheath fluid to enter the flow path 110 at a sheath fluid input 114, creating a flow 116 of sheath fluid through the flow path 110. Downstream from the sheath fluid input 114 and preferably in a region of smooth, laminar flow of the sheath fluid, an analyte fluid input tube 118 allows a stream 120 of analyte fluid (i.e., a fluid in which an analyte is suspended, carried, etc.) to enter the flow path 110 through an analyte input 122. In some embodiments, the analyte input 122 is disposed centrally within the flow 116 of sheath fluid and/or centrally within the flow path 110, and oriented such that the stream 120 of analyte fluid is parallel to the flow 116 of sheath fluid as the analyte fluid enters the flow path 110. Of course, the analyte input 122 need not be central to either of the flow 116 of sheath fluid or the flow path 110, and one of ordinary skill in the art could envision embodiments in which the stream 120 of analyte fluid is other than parallel to the flow 116 of sheath fluid as the stream 120 of analyte fluid enters the flow path 110. The flow rate and pressure of the flow 116 of sheath fluid relative to the stream 120 of analyte fluid compress and constrict the stream 120 of analyte fluid to be narrow relative to the flow 116 of the sheath fluid. The flow 116 of sheath fluid and the stream 120 of analyte fluid combine to form a sample flow 123.

The flow path 110 may change direction in a region 124, but preferably thereafter includes a region 126 free of both obstacles and abrupt changes in flow direction, and serving to stabilize the sample flow 123 before the sample flow 123 reaches an interrogation area 128 (i.e., an observation area, analysis area, nominal focal point, etc.). The path of the sample flow 123 through the flow path 110 defines a flow axis 130. In some embodiments, the stream 120 of analyte fluid and, in particular, the analytes (i.e., the cells) within the stream 120 of analyte fluid generally travels through the flow path 110 along the flow axis 130.

After reaching and/or passing through the interrogation area 128, the sample flow 123 is diverted. In some embodiments, the flow path 110 changes directions at a corner 132 (indicated in FIG. 2 by a broken line). In other embodiments, the sample flow 123 encounters a transverse flow 134 as it reaches an end 136 of the region 126. The transverse flow 134 redirects the sample flow 123. In some embodiments, the corner 132 or the transverse flow 134 causes a 90-degree change in the direction of the sample flow 123. However, the sample flow 123 may, in alternative embodiments, vary by more or less than 90 degrees. In any event, after changing direction, the sample flow 123 may flow to a collection vessel 138, and may pass through one or more flow path elements 140 (e.g., flow regulators, filters, etc.) before reaching the collection vessel 138.

An objective lens 142 disposed generally at or near the corner 132 or at or near the intersection of the sample flow 123 with the transverse flow 134 operates to create a focal point (not shown) within the interrogation area 128. An optical axis 144 of the objective lens 142 is generally coaxially aligned with the flow axis 130 of the flow path 110 as the flow path 110 passes through the interrogation area 128. Of course, the optical axis 144 and the flow axis 130 need not be perfectly coaxial, and may vary such that the optical axis 144 is parallel to and offset from the flow axis 130, such that the optical axis 144 is at an oblique angle with respect to the flow axis 130, etc.

Figure 3:
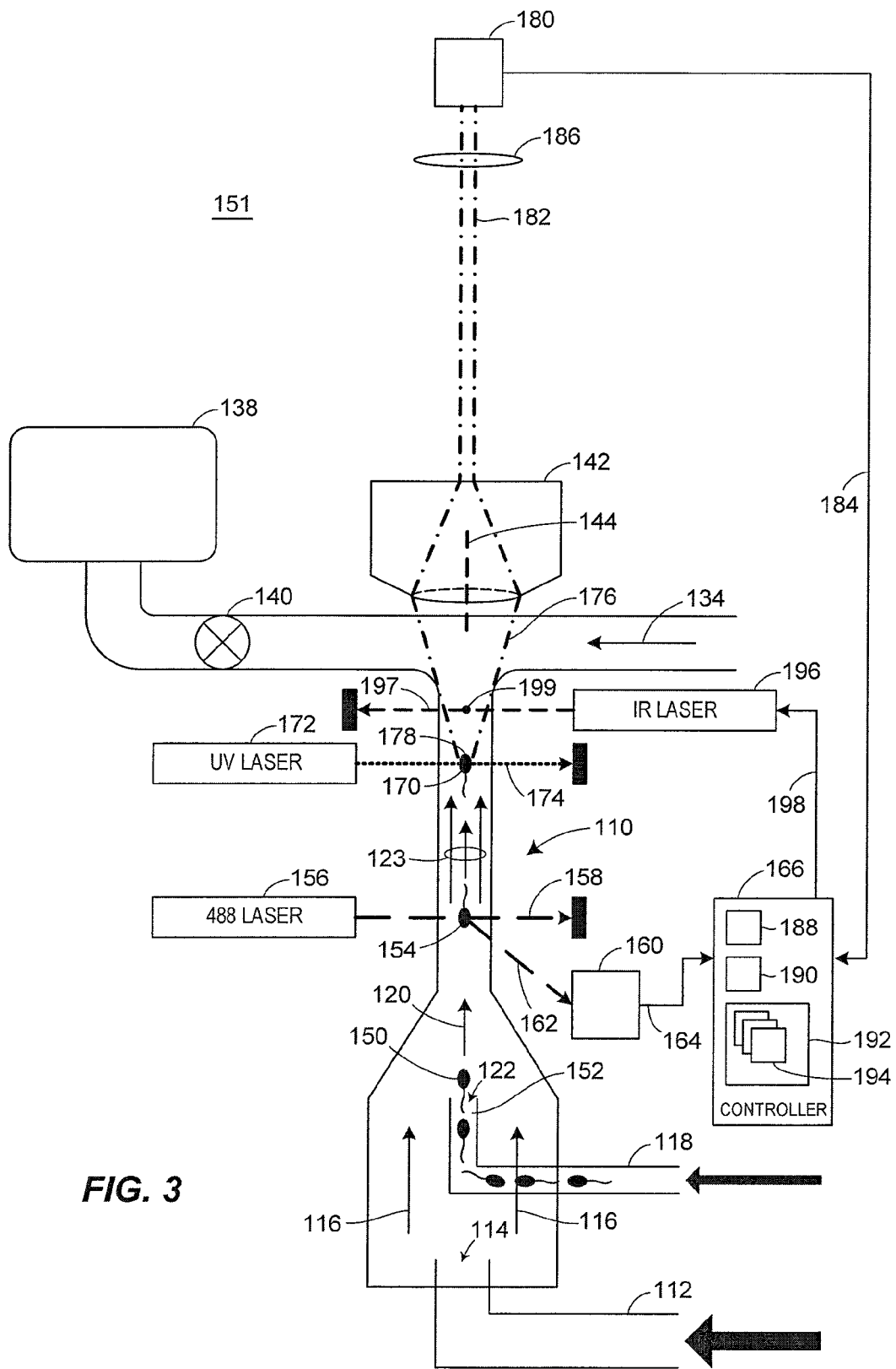
FIG. 3 depicts a contemplated embodiment of a sorting flow cytometer.

FIG. 3 illustrates an exemplary sorting flow cytometer 151 including various characteristics of the described methods and apparatus. Similarly to the embodiment of the flow path 110 depicted in FIG. 2, FIG. 3 depicts the sheath flow input tube 112 and the sample fluid input tube 118, introducing respectively the flow 116 of sheath fluid and the stream 120 of analyte fluid through the sheath fluid input 114 and the analyte fluid input 122. In particular, the analyte fluid depicted in FIG. 3 includes mammalian sperm cells 150 and a buffer solution 152 carrying the mammalian sperm cells 150. As the flow 116 of sheath fluid and the flow 120 of analyte fluid merge to form the sample flow 123, the respective flow rates cause the cells 150 to form a generally single-file stream and to align their lengthwise axis (i.e., along the length of the cells' tail) with the direction of the sample flow 123.

Referring still to FIG. 3, an embodiment of a sorting flow cytometer includes a first analysis and a second analysis. As the cells 150 proceed through the flow path 110 with the sample flow 123, the first analysis may determine whether the cells are of interest, may determine the rate at which the cells are moving through the flow path 110, may determine whether, at a given point in the sample flow 123, the cells 150 are too close together for one or more later analyses, whether the cells 150 are oriented tail-first or head-first, etc. In the embodiment depicted by FIG. 3, the first analysis occurs as the cells 150 reach a point 154 in the flow path 110. A first analysis illumination source 156 directs energy 158 toward the point 154. The energy 158 may interact with each cell 150 to scatter the energy 158 or to otherwise interact with the cell 150, an antibody associated with the cell 150, a fluorochrome (e.g., fluorescein) associated with the cell 150, etc. A detector 160 may detect resulting energy 162 (e.g., the scattered energy, the resulting fluorescent signal, etc.) and send a corresponding signal via a connection 164 to a controller 166. The detector 160 may be disposed at any location appropriate to detect the energy 162, including at an oblique angle from the point 154 (with respect to the illumination energy source 156) or in line with the point 154. The first analysis illumination source 156 is preferably a 488 nm laser, but may comprise any energy source suitable for the measurements contemplated in the first analysis. The first analysis illumination source 156 may be oriented such that the energy 158 travels perpendicularly to the sample flow 123 or may, alternatively, be oriented such that the energy 158 is incident upon the cells 150 at an oblique angle to the direction of the sample flow 123. Moreover, the energy 158 and/or the energy 162 may pass through one or more optical elements (not shown) such as filters, lenses, etc., which may allow either or both of the illumination energy source 156 and the detector 160 to be positioned differently than depicted by creating a different optical path as generally known in the art.

Some embodiments may omit the first analysis. For example, information gleaned from the second analysis (described in detail below) may prove sufficient both to determine which cells are of interest and to distinguish between cells in desired and un-desired sub-populations. Thus, the elements 154-164 may be omitted in some embodiments. Alternatively, some embodiments may include two or more first analyses and, accordingly, two or more sets of elements 154-164. For example, and without limitation, the sample flow 123 may include one or more markers (e.g., included in the sheath flow 116, attached or otherwise associated with some cells 150 in the sample stream 120, etc.). A primary first analysis may detect one of the markers at a first point, and a secondary first analysis may detect the marker at a second point to determine the flow rate of cells in the sample flow 123.

In any event, the sample flow 123 proceeds after the first analysis to carry the cells 150 along the flow path 110. As the cells 150 pass through a point 170, the second analysis characterizes the cells 150, as described below, to determine whether to modify each cell 150. As each cell 150 reaches the point 170, a second analysis illumination source 172 directs energy 174 toward the point 170. The energy 174 may interact with the cell 150, an antibody associated with the cell 150, a fluorochrome (e.g., Hoechst stain) associated with the cell 150 or with DNA within the cell 150, etc. In some embodiments, the second analysis illumination source 172 is an ultraviolet laser emitting the energy 174 in the form of ultraviolet radiation that interacts with particles of Hoechst stain attached to the DNA inside of the cell 150 to cause fluorescence proportional to the DNA content of the cell 150, as generally known in the art. The second analysis illumination source 172 may be oriented such that the beam 174 is perpendicular to the sample flow 123, as depicted in FIG. 3. However, the second analysis illumination source 172 may also be located at an oblique angle with respect to the sample flow 123. Moreover, the energy 174 may pass through one or more optical elements (not shown) such as filters, lenses, etc., which may allow the second analysis illumination source 172 to be positioned differently than depicted by creating an optical path that is not straight.

The interaction of the energy 174 with the cell 150 or with elements inside the cell 150, causes resulting energy 176 to radiate from the cell 150. The objective lens 142, positioned such that the optical axis 144 of the objective lens 142 is generally coaxial with the sample flow 123, operates to focus the energy 176. A focal point 178 of the objective lens 142 is located generally at the point 170, but may be located so as to detect the resulting energy 176 from the cell 150 slightly after the energy 174 illuminates the cell 150 (i.e., the focal point 178 may be slightly closer to the objective lens 142 than the point 170). A detector 180 situated so as to receive energy 182 focused by the objective lens 142 detects the focused energy 182 from the cell 150, and sends a corresponding signal via a connection 184 to the controller 166. Of course, one or more optical elements, such as a filter 186 may act to alter or redirect the energy 182 between the objective lens 142 and the detector 180. In some embodiments, the objective lens 142 creates the focal point 178 prior to the corner 132 or the convergence of the transverse flow 134 and the sample flow 123. In other embodiments, the objective lens 142 creates a focal point (not shown) at or near the corner 132 or the convergence of the transverse flow 134 and the sample flow 123.

The controller 166, which may include one or more microprocessors 188, one or more crystal oscillators 190, one or more memories 192 storing one or more routines 194, etc., interprets the signals received from the detector 160 and/or the detector 180, to determine for each cell 150 whether the cell 150 is part of a desired sub-population of cells. For example, in some embodiments, the cells 150 are mammalian sperm cells, and the controller 166 interprets signals received from the detector 180 to determine whether each cell 150 bears an X chromosome or a Y chromosome. As generally known by those of ordinary skill in the art, in mammalian sperm cells Y chromosomes generally contain less DNA than X chromosomes. Accordingly, by analyzing the fluorescence (i.e., the resulting energy 176) emitted by the stain in the cell 150 upon illumination by the second analysis illumination source 172, the controller 166 may generally determine whether the cell 150 carries an X or a Y chromosome. In some embodiments, one of the routines 194 continuously monitors the statistical distribution of detected fluorescent signals to improve with the passage of time the accuracy of the determination.

Still referring to FIG. 3, in some embodiments, the controller 166, according to the determination of whether a cell 150 is part of a desired sub-population, outputs a signal to a controllable energy source 196 via a connection 198. The controllable energy source 196 may emit energy 197 directed at a point 199 in the sample flow 123. In some embodiments, the controller 166 operates to coordinate the signal to the controllable energy source 196 and/or the point 199 is selected (e.g., by aiming, by one or more lenses, mirrors, etc.) according to the rate at which the cell 150 moves through the flow path 110. In some embodiments, the point 199 may be located prior to the corner 132 or the convergence of the transverse flow 134 and the sample flow 123, to simplify the determination of the position of the cell 150 traveling along the flow path 110. In other embodiments, the point 199 may be located after the corner 132, or may be located at or after the convergence of the transverse flow 134 and the sample flow 123. In the example above, the controller 166 may output a signal to cause the controllable energy source 196 to emit the energy 197 in response to a determination that the cell 150 has an X chromosome or in response to a determination that the cell 150 has a Y chromosome. Alternatively, the controller 166 may output a signal to cause the controllable energy source 196 to stop emitting energy 197 in response to a determination that the cell 150 has an X chromosome or in response to a determination that the cell 150 has a Y chromosome. The energy 197 emitted from the controllable energy source 196 may act to disable the cell 150 or render the cell 150 non-viable (e.g., by modifying cellular components or chemicals including proteins, DNA, and substances involved in cellular metabolism; by causing disruption, heating, cavitation, or explosions in or near the cell 150; by causing permeabilization or perforation of the cell 150; and/or by causing destruction, fragmentation, or morphological alteration of the cell 150), may act to alter (e.g., by interacting with a chemical in or attached to a cellular component) the cell so that it may later be identified and/or removed from the desired sub-population of cells 150, or may act to favorably affect the cell. In some embodiments, the controllable energy source 196 is a laser and, in particular, may be a laser outputting energy in the visible or infrared parts of the spectrum. In some embodiments, the laser outputs energy having a wavelength of 690 nm. In other embodiments, the controllable energy source 196 may output other types or wavelengths of radiation, such as X-rays, microwaves, visible light, infrared light, ultraviolet light, or any other type of energy having a desired effect on a cell 150. Of course, in response to the determination of whether a cell is part of the desired sub-population the controller 166 may: (1) emit energy 197 to adversely affect cells 150 determined not to be part of the desired sub-population (while leaving alone cells 150 determined to be part of the desired sub-population); (2) may emit energy 197 to positively affect cells 150 determined to be part of the desired sub-population (while leaving alone cells 150 determined not to be part of the desired sub-population); (3) may stop emitting energy 197 to avoid positively affecting cells 150 determined not to be part of the desired sub-population (while continuing to emit energy 197 to positively affect cells 150 determined to be part of the desired sub-population); or (4) may stop emitting energy 197 to avoid adversely affecting cells 150 determined to be part of the desired sub-population (while continuing to emit energy 197 to adversely affect cells 150 determined not to be part of the desired sub-population). Moreover, in some embodiments, the controller 166 may treat indeterminate cells 150 (e.g., cells 150 for which the controller 166 cannot make a determination, cells 150 that are too close together, etc.) in the same manner in which the controller 166 treats cells determined not to be in the desired sub-population.

Figure 4:
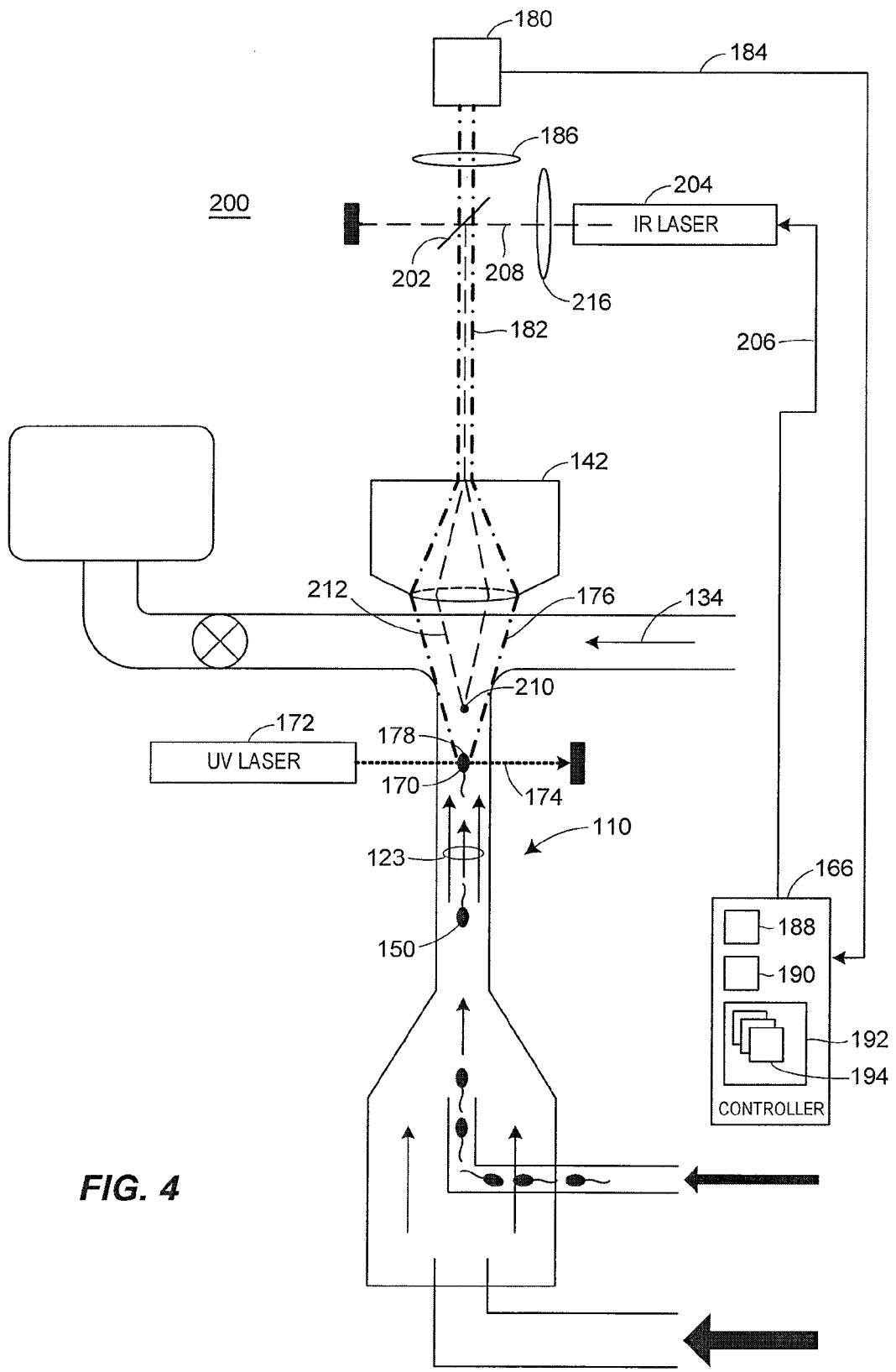
FIG. 4 depicts a contemplated alternate embodiment of a sorting flow cytometer.

FIG. 4 illustrates an exemplary sorting flow cytometer 200 including various characteristics of the described methods and apparatus. In particular, the sorting flow cytometer 200 depicted in FIG. 4 omits the first analysis and, accordingly, the elements 154-164 do not appear. However, while not illustrated, those of ordinary skill in the art will appreciate that the first analysis may be included, if desired, in the embodiment illustrated in FIG. 4. As in the embodiment depicted in FIG. 3, the sample flow 123 carries the cells 150 along the flow path 110. As the cells 150 pass through the point 170, the second analysis (which, in the depiction of FIG. 4 does not follow any first analysis) characterizes the cells 150, as described above, to determine whether to modify each cell 150. That is, as each cell 150 reaches the point 170, the second analysis illumination source 172 directs the energy 174 toward the point 170, and the energy 174 interacts with the cell 150, as described above. Of course, the second analysis illumination source 172 may be an ultraviolet laser and the energy 174 may interact with molecules of Hoechst 33342 stain attached to the DNA inside of the cell 150. The second analysis illumination source 172 may be oriented such that the beam 174 is perpendicular to the sample flow 123, as depicted in FIG. 4. However, the second analysis illumination source 172 may also be at an oblique angle with respect to the sample flow 123. Moreover, the energy 174 may pass through one or more optical elements (not shown) such as filters, lenses, etc., which may allow the second analysis illumination source 172 to be positioned differently than depicted by creating an optical path that is not straight.

The resulting energy 176 radiating from the cell 150 propagates toward the objective lens 142, which is positioned such that the optical axis 144 (see FIG. 3) of the objective lens 142 is generally coaxial with the sample flow 123, and operates to focus the energy 176. The focal point 178 of the objective lens 142 is located generally at the point 170, but may alternatively be located so as to detect the resulting energy 176 from the cell 150 slightly after the energy 174 illuminates the cell 150. One or more optical elements may direct the focused energy 182 from the objective lens 142 to the detector 180. For example, in the embodiment depicted by FIG. 4, the focused energy 182 passes through a beam splitter 202 and the filter 186 before reaching the detector 180. Other optical elements (e.g., lenses, mirrors, filters, etc.) may also affect the path of the focused energy 182 between the objective lens 142 and the detector 180. As in the embodiment depicted in FIG. 3, in some embodiments the objective lens 142 creates the focal point 178 prior to the corner 132 or the convergence of the transverse flow 134 and the sample flow 123. In other embodiments, the objective lens 142 creates a focal point (not shown) at or near the corner 132 or the convergence of the transverse flow 134 and the sample flow 123.

The controller 166, as described above with respect to FIG. 3, operates to interpret signals received (via the connection 184) from the detector 180 (and the detector 160 if the cytometer 200 includes the first analysis) to determine for each cell 150 whether the cell 150 is part of a desired sub-population of cells (e.g., sperm cells with an X chromosome). The controller 166 outputs a signal over a connection 206 to a controllable energy source 204. The controllable energy source 204 operates in the same manner as the controllable energy source 196 (FIG. 3). However, in the embodiment depicted in FIG. 4, energy 208 emitted by the controllable energy source 204 passes through the objective lens 142 after passing, in some embodiments, through one or more optical elements, such as a filter 216. The objective lens 142 operates to focus the energy 208 at a focal point 210. In some embodiments, the objective lens 142 may focus the energy 208 from the controllable energy source 204 such that the focused energy 212 is generally coaxial with the sample flow 123, and such that the point 210 is located closer to the objective lens 142 than the point 170.

Figure 7:
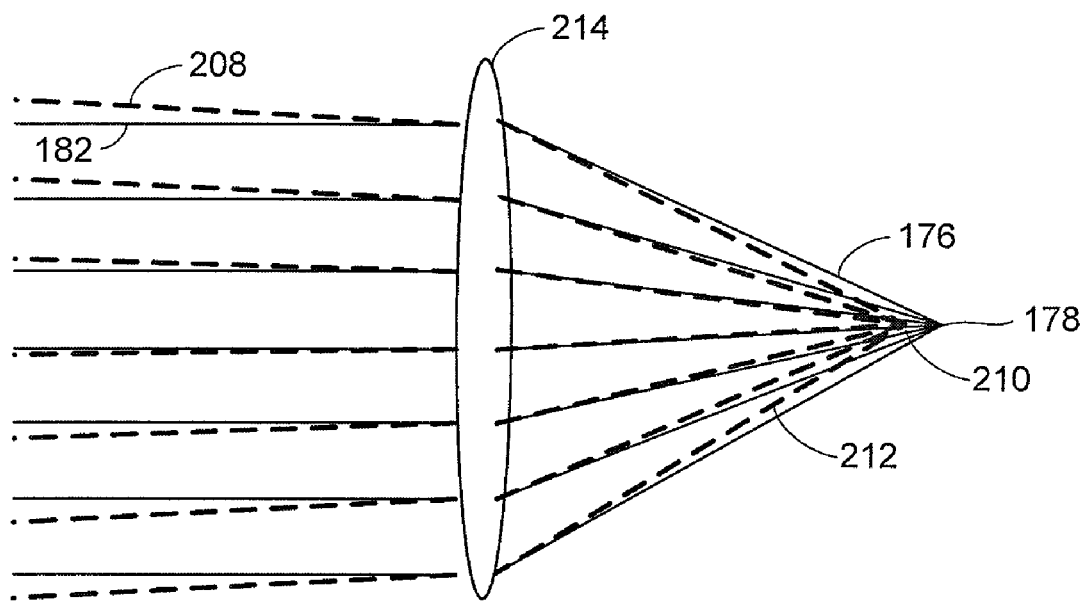
FIG. 7 illustrates a method that may be used with one or more embodiments of a contemplated sorting flow cytometer to create two different focal points for energy within the system.

Those of ordinary skill in the art will appreciate that multiple methods exist for creating both the focal point 210 and the focal point 178 using the same lens. FIG. 7 depicts one method that the cytometer 200 could employ to create the focal point 178 for the energy 176 and the focal point 210 for the energy 212. FIG. 7 depicts that as the energy 176 (indicated by solid lines in FIG. 7) passes through a lens 214 of the objective lens 142 (not shown in FIG. 7) from the focal point 178 (i.e., from the cell 150 at the point 170), the lens 214 acts on the energy 176 such that the rays of energy 176 are parallel as they leave the lens 214. By contrast, the rays of energy 208 are converging slightly as they fall incident upon the lens 214 and, accordingly, converge at the focal point 210 after passing through the lens 214. Of course, other methods exist for creating both the focal point 178 and the focal point 210, including taking advantage of the fact that different wavelengths of energy may refract differently through the same material, or employing multi-focal lenses such as, by way of example and not limitation, those described in U.S. Pat. No. 6,010,647.

Figure 5:
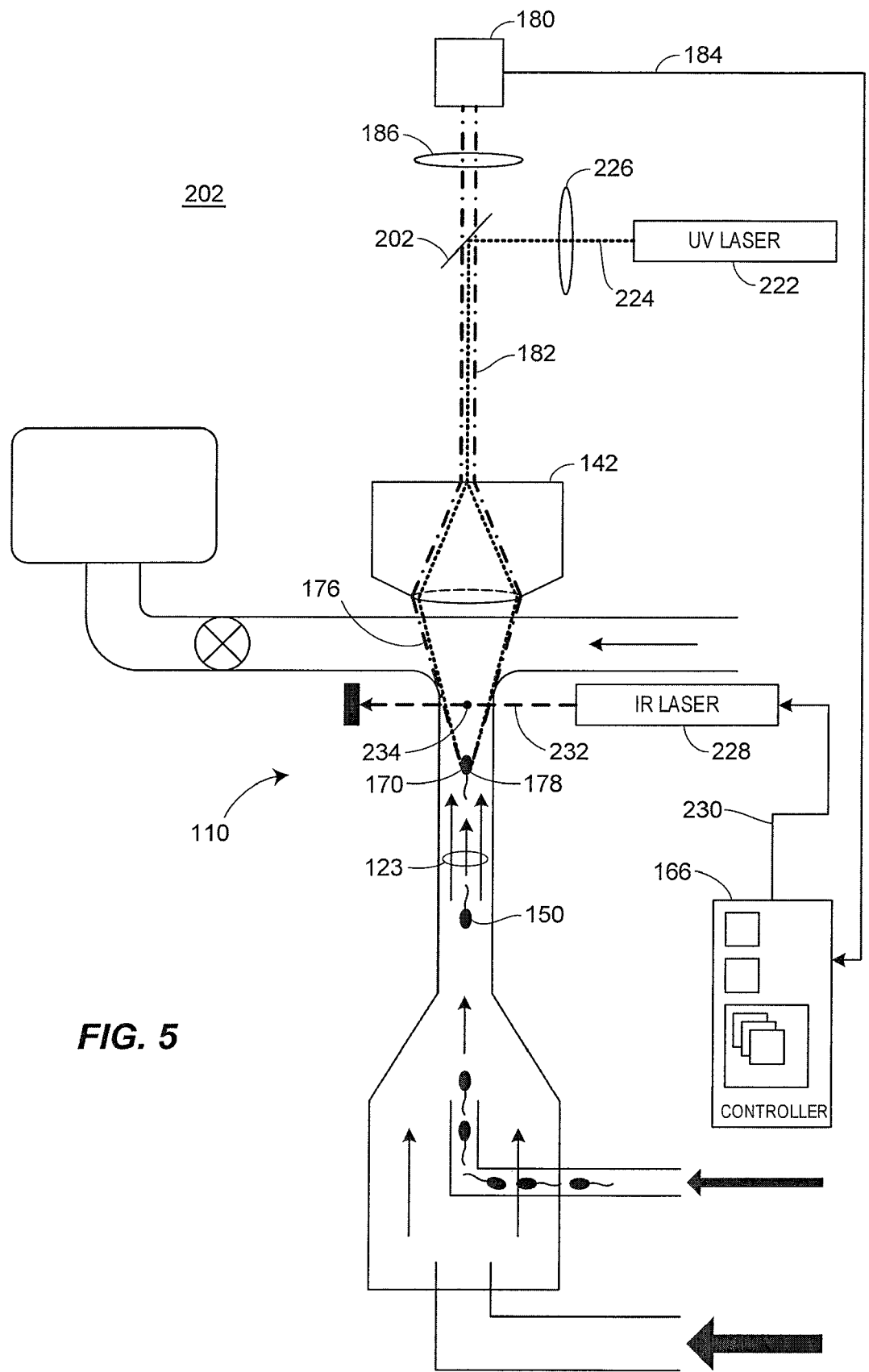
FIG. 5 depicts another contemplated alternate embodiment of a sorting flow cytometer.

For illustrative purposes, FIG. 5 depicts another exemplary embodiment of a sorting flow cytometer 220. The sorting flow cytometer 220 includes the flow path 110 as generally described with respect to FIGS. 3 and 4. Similarly to the sorting flow cytometer 200 depicted in FIG. 4, the sorting flow cytometer 220 omits the first analysis (as well as equipment associated with the first analysis). The sample flow 123 and, in particular, the cells 150, flow toward the objective lens 142. As in previously-described embodiments, the objective lens 142 creates a focal point 178 at a point 170 in flow path 110. The energy 176 from the cell 150 as the cell 150 reaches the point 170 passes through the objective lens 142, which objective lens 142 is positioned such that the optical axis 144 of the objective lens 142 is generally coaxial with the sample flow 123, and operates to focus the energy 176. The focal point 178 of the objective lens 142 is located generally at the point 170, but may alternatively be located so as to detect the resulting energy 176 from the cell 150 slightly after the energy 174 illuminates the cell 150. One or more optical elements (such as the beam splitter 202, the filter 186, etc.) may direct the focused energy 182 from the objective lens 142 to the detector 180.

Referring still to FIG. 5, the depicted sorting flow cytometer 220 includes a second analysis illumination source 222. The second analysis illumination source 222 emits energy 224, which may be ultraviolet energy 174. The energy 224 emitted from the second analysis illumination source 222 travels through an optical path to the objective lens 142. The objective lens 142 may focus the energy 224 on the focal point 178 and, in this manner, the optical paths of the energy 176 and the energy 224 may overlap to some degree. Various arrangements of other optical elements, such as the beam splitter 202 and a filter 226 may operate to direct the energy 224 from the second analysis illumination source 222 to the objective lens, and to direct the energy 176 (from the cell 150) from the objective lens 142 to the detector 180.

The controller 166, as described above with respect to FIGS. 3 and 4, operates to interpret signals received (via the connection 184) from the detector 180 (and the detector 160 if the cytometer 200 includes the first analysis) to determine for each cell 150 whether the cell 150 is part of a desired sub-population of cells. The controller 166 outputs a signal over a connection 230 to a controllable energy source 228. The controllable energy source 228 operates in the same manner as the controllable energy source 196 (FIG. 3), outputting energy 232 directed at a point 234.

Figure 6A:
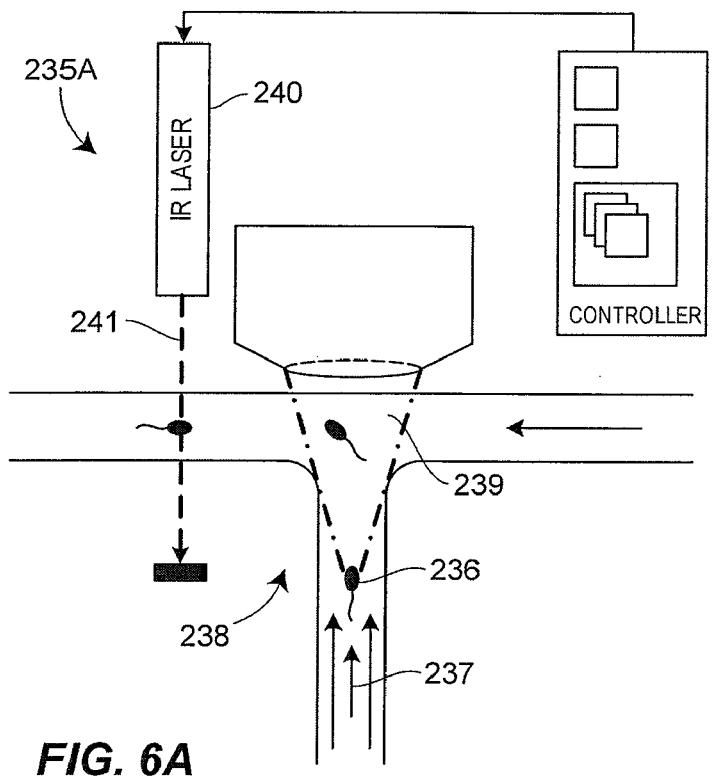
FIG. 6A depicts a contemplated alternate embodiment of a portion of a sorting flow cytometer.
Figure 6B:
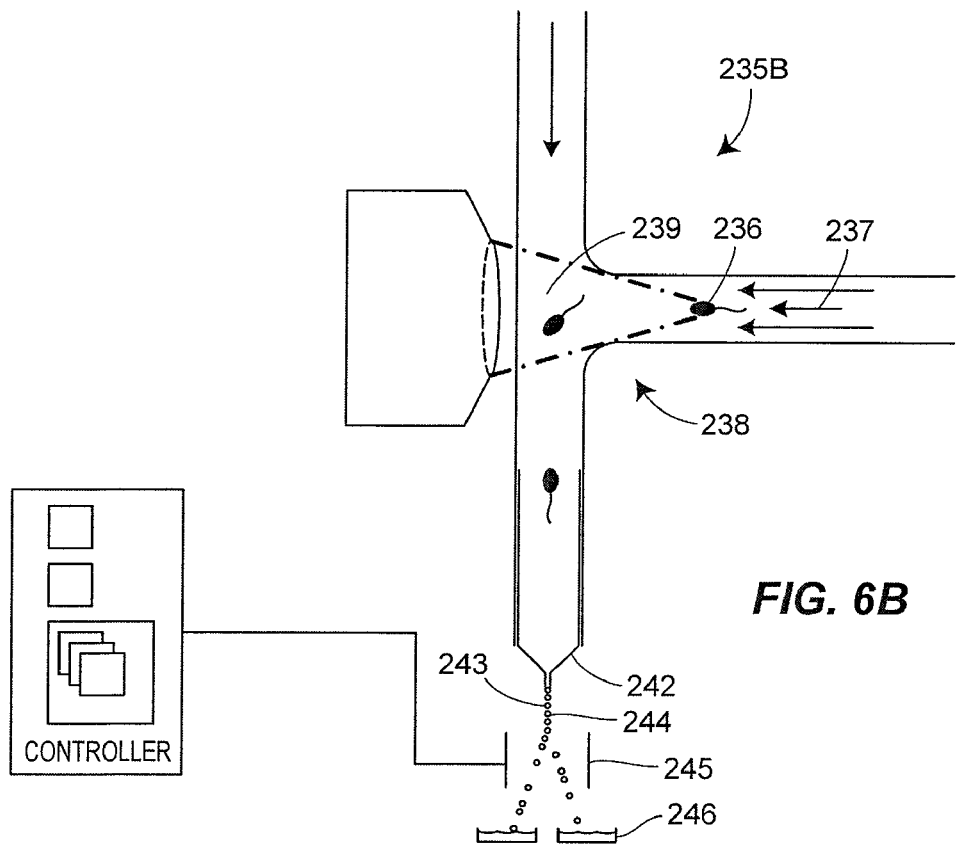
FIG. 6B depicts another contemplated alternate embodiment of a portion of a sorting flow cytometer.

FIGS. 6A and 6B depict portions 235A and 235B, respectively, of still other embodiments of a flow cytometer in accordance with the contemplated methods and apparatus. In each of FIGS. 6A and 6B, cells 236 travel in a stream 237 through a flow path 238, which flow path 238 changes trajectory at or around a point 239, as described with respect to FIG. 2. Fluidics modeling of and/or precise formation of the flow path 238 and/or the stream 237 of cells 236 through the flow path 238, and/or the inclusion of additional elements (not shown) to monitor the position of cells 236, may ameliorate uncertainty otherwise caused by the change in trajectory at or around the point 239. In this way, the position and identity of individual cells may remain determinable after the trajectory change. FIG. 6A depicts an embodiment in which a controllable energy source 240, operating in the same manner as described above with respect to FIGS. 3, 4, and 5 (196, 204, and 228, respectively) is positioned such that emitted energy 241 falls incident upon cells 236 after the cells 236, travel past the point 239 in the flow path 238. FIG. 6A depicts the energy 241 traveling perpendicularly to the direction in which the cells 236 flow through the flow path 238. Of course, one may appreciate that the controllable energy source 240 may alternatively be positioned such that the emitted energy 241 travels generally coaxially with the direction in which the cells 236 flow through the flow path 238 (e.g., by again changing the flow direction, and positioning the controllable energy source 240 such that the cells 236 in the flow path 238 travel toward the controllable energy source 240).

It should be appreciated that a sorting flow cytometer in accordance with the contemplated methods and apparatus may alternatively employ a "jet-in-air" configuration, as depicted in FIG. 6B. FIG. 6B depicts a nozzle 242 emitting a stream 243 of droplets 244. A controllable energy source (not shown) selectively alters droplets by imparting a charge to one or more of the droplets 244. Thereafter, and by way of example and not limitation, a pair of electrically charged plates 245 may sort the stream 243 of droplets 244 into receptacles 246 according to a determination by a detector (not shown), as described above.

Figure 8A:
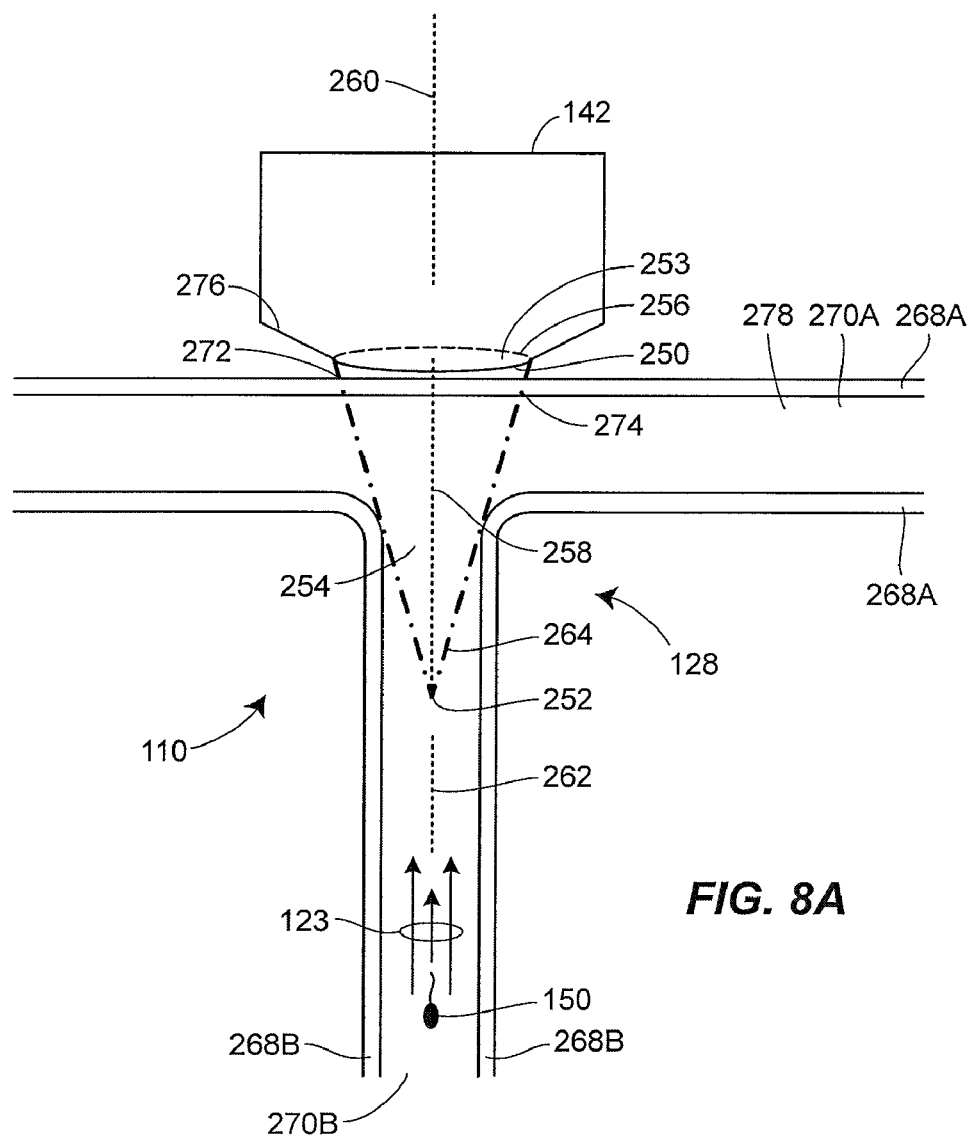
FIG. 8A depicts an objective lens and associated focal point within a flow path of a contemplated embodiment of the presently described methods and apparatus.

FIG. 8A depicts the objective lens 142 and a portion of the flow path 110 that includes the interrogation region 128. As generally known in the art, one or more lens elements 250 (e.g., a hemispherical front lens, a meniscus lens, etc.) act to create a nominal focal point 252. In the embodiments described above with respect to FIGS. 3-5, the nominal focal point 252 is within the sample flow 123 and, in particular, within the path of the cells 150 through the flow path 110. The nominal focal point 252 defines the apex of a generally conical volume 254 between the nominal focal point 252 and an outer element 256 of the objective lens 142 forming a base 253 of the conical volume 254. The conical volume 254 may be a right circular conical volume, but may also be an oblique conical volume. An axis 258 of the cone is generally coaxial with an axis 260 of the objective lens 142 in embodiments in which the conical volume 254 is a right circular conical volume. In such embodiments, the axes 258 and 260 are further coaxial with an axis of flow 262 within the flow path 110, which axis of flow 262 generally defines the path that the cells 150 travel within the flow path 110.

Figure 8B:
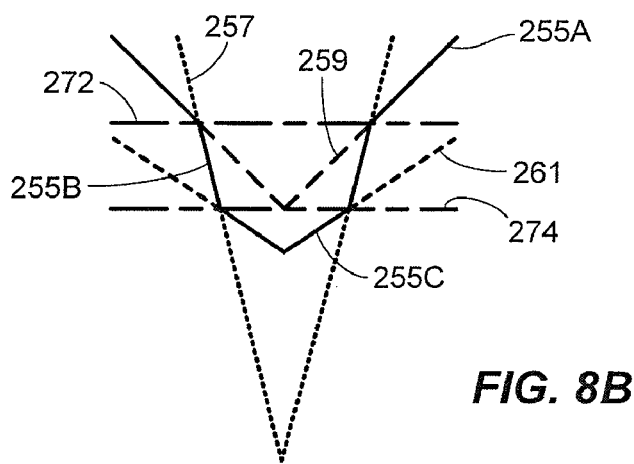
FIG. 8B illustrates an embodiment of a generally conical volume formed between a nominal focal point and an objective lens.

In some embodiments, the focal point 252 of the objective lens 142 is such that the number of interfaces through which the lateral surface 264 of the conical volume 254 passes is minimized. For example, and with reference to FIG. 8A, flow path wall 268A forms the a generally cylindrical transverse flow path 270A, and flow path wall 268B forms a generally cylindrical flow path 270B that is generally coaxial with the axis of the conical volume 254. The conical volume 254 in FIG. 8A passes through only two interfaces as it enters and exits the material comprising the wall 268A. The conical volume 254 passes through an interface 272 between air 276 and the material comprising the wall 268A, and through an interface 274 between the material comprising the wall 268A and fluid 278 in the flow path 110. Moreover, in some embodiments, the wall 268A of the flow path 110 through which the lateral surface 264 passes may be generally parallel to the base 253 of the conical volume 254. This simplifies the interfaces through which the energy focused by the objective lens 142 must pass (i.e., the energy does not pass through any curvilinear surfaces), each of which interfaces may, by operation of refraction, affect the focal point 252 of the objective lens 142. Further, the conical volume 254 may be formed of sections 255A, 255B, and 255C of multiple cones 257, 259, and 261 joined together, as shown in FIG. 8B, such as is the case where one or more interfaces (such as the interfaces 272 and 274) are formed of materials having differing refractive indices.

Figure 9:
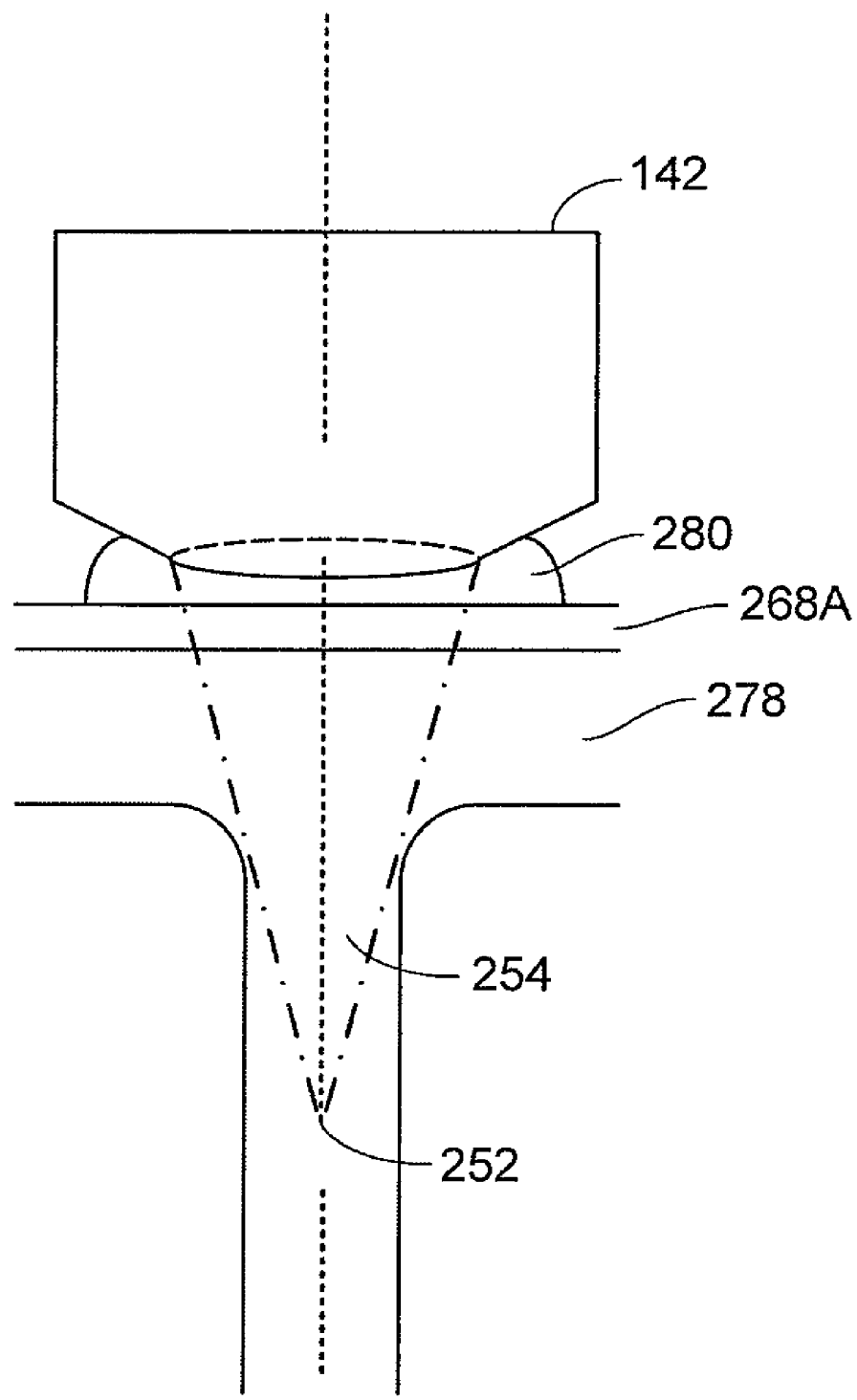
FIG. 9 depicts a water immersion objective lens and associated focal point within a flow path of an embodiment of the presently described methods and apparatus.

Generally, the conical volume 254 must pass through at least the two interfaces 272 and 274. In some embodiments of the described methods and apparatus, the objective lens 142 may take account of one or more of the interfaces, for example by accounting for a thickness and refractive index of the material forming the interfaces (e.g., the wall 268A). Moreover, in some embodiments, the objective lens 142 may be a water-dipping, water-immersion, or oil-immersion lens, which uses an immersion medium (e.g., water or oil) having a refractive index similar to that of the material forming the interface (e.g., the wall 268A). Thus, as depicted in FIG. 9, some embodiments further reduce distortion of the focal point 252 by minimizing differences between the respective refractive indices of the materials through which the conical volume 254 passes. In FIG. 9, for example, the conical volume 254 may pass through water 280, the wall 268A, and the fluid 278 in the flow path 110. The objective lens 142 may be a water-immersion objective lens where, for example, the wall 268A is made of glass. Alternatively, the objective lens 142 may be a water-dipping lens in situations in which there is no need to correct for refraction caused by the wall 268A, such as when the wall 268A is formed of a material with a refractive index similar to or the same as the fluid 278.

In still further embodiments, and as described fully in concurrently-filed application Ser. No. 12/495,437, the walls 268A and 268B of the flow path 110 may be formed of material having a refractive index close to that of the fluid 278 (i.e., a material that minimizes the difference between refractive indices of the materials through which the conical volume 254 passes). For example, materials having a refractive index close to that of water include materials with a refractive index in the range of 1.30 to 1.40, inclusive. Several solid materials in the families of amorphous perfluoropolymers, amorphous fluoropolymers, and perfluoroalkoxy polymers have refractive indices in that range. By way of example and not limitation, Cytop™, manufactured by Asahi Glass Co., Ltd., and Teflon® AF and Teflon® PFA, manufactured by DuPont™, are three such materials.

In some embodiments, the methods or apparatus may also adjust the refractive index of the fluid 278 such that the refractive index of the fluid 278 is closer to the refractive index of the material forming the walls 268A and/or 268B of the flow path 110. In particular, the methods or apparatus may adjust the refractive index of the fluid 278 to be within 0.02 of the refractive index of the material forming the walls 268A and/or 268B of the flow path 110.

Figure 10:
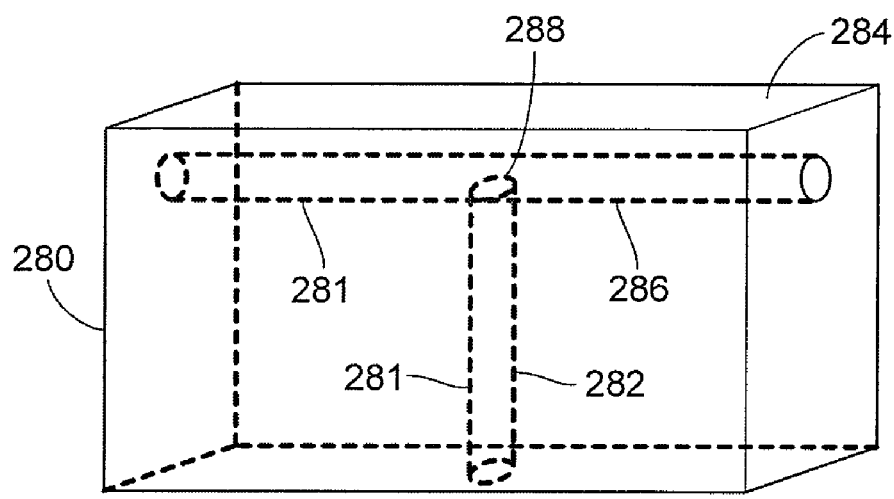
FIG. 10 depicts a body in which a portion of the flow path of a sorting flow cytometer may be formed, in accordance with an embodiment of the presently described methods and apparatus.

In some cytometers, a portion of the flow path 110, including the interrogation region 128, is formed in a body 280, such as the body 280 shown in FIG. 10. FIG. 10 depicts the body 280 as a rectangular cuboid, having drilled or otherwise formed therein a portion 281 of the flow path 110. The portion 281 includes a first flow path portion 282 generally perpendicular to a surface 284 through which the objective lens 142 may observe, and a second flow path portion 286 generally parallel to the surface 284 and intersecting an end 288 of the first flow path section 282 nearest the surface 284. The body 280, which may, for example, be a cuvette, may be formed of polished quartz, glass, plastic, or other materials as generally known in the art. In some embodiments, the body 280 may be formed, in whole or in part, of a material having a refractive index in the range of 1.30 to 1.40, inclusive, such as Cytop™ or Teflon® AF.

Figure 11:
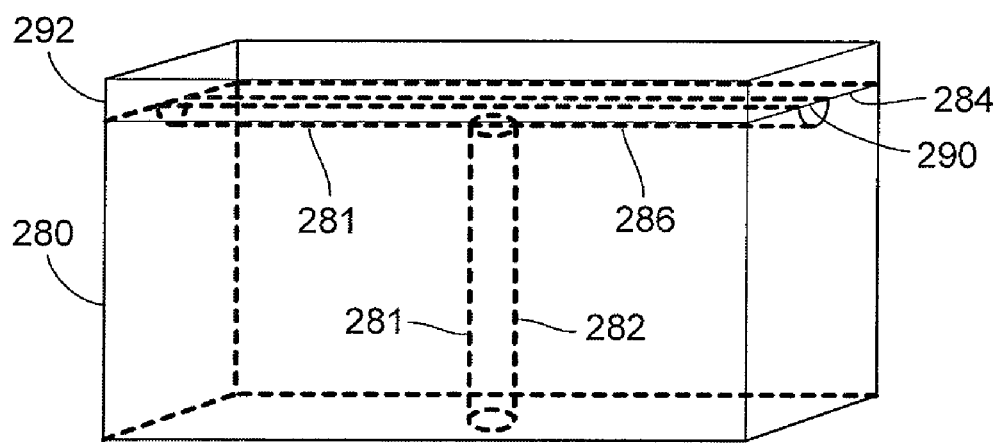
FIG. 11 depicts an alternate embodiment of the body depicted in FIG. 9.

In another embodiment, illustrated in FIG. 11, the body 280 includes the portion 281 of the flow path. The portion 281 includes the first flow path portion 282 generally perpendicular to the surface 284 through which the objective lens 142 may observe. However, in the embodiment depicted in FIG. 11, the second flow path portion 286 forms a channel having an upper edge 290 generally coplanar with the surface 284. A coverslip 292 disposed on top of the surface 284 may, in some embodiments, allow the use of an objective lens corrected for use with such a coverslip 292 to eliminate or minimize the refractive effects of interfaces between materials with differing refractive indices.

Figure 12:
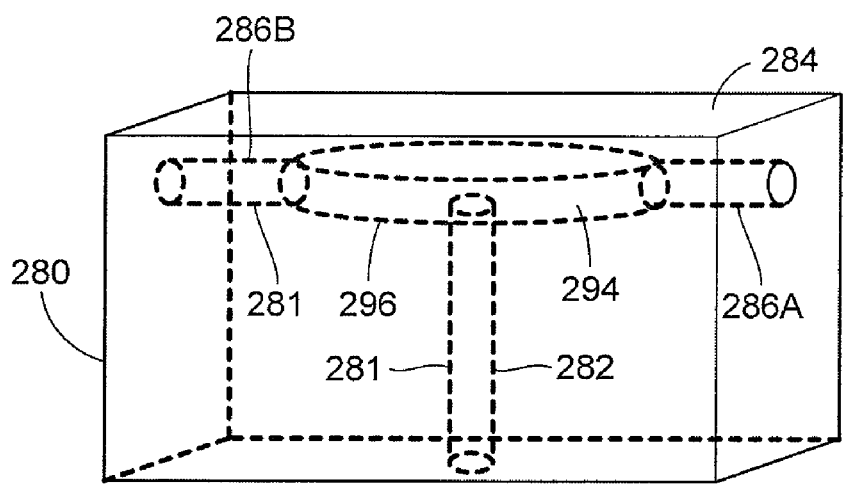
FIG. 12 depicts another alternate embodiment of the body depicted in FIG. 9.

In still other embodiments, such as that depicted in FIG. 12, the body 280 includes a reservoir 294 formed at the intersection of first flow path portion 282 and the second flow path portion 286. For example, the first flow path portion 282 may intersect the reservoir 294 at a generally planar bottom surface 296 that is generally parallel to the surface 284. Two parts 286A and 286B of the flow path portion 286 may connect to the reservoir 294 at opposing surfaces of the reservoir 294, which may generally have the shape of a flattened cylinder. This arrangement may provide further flexibility when adjusting the focal point 252 (FIGS. 8 and 9) by, for example, preventing the conical volume 254 from passing through the wall 268A of the generally cylindrical transverse flow path 270A (FIGS. 8 and 9).

Figure 13:
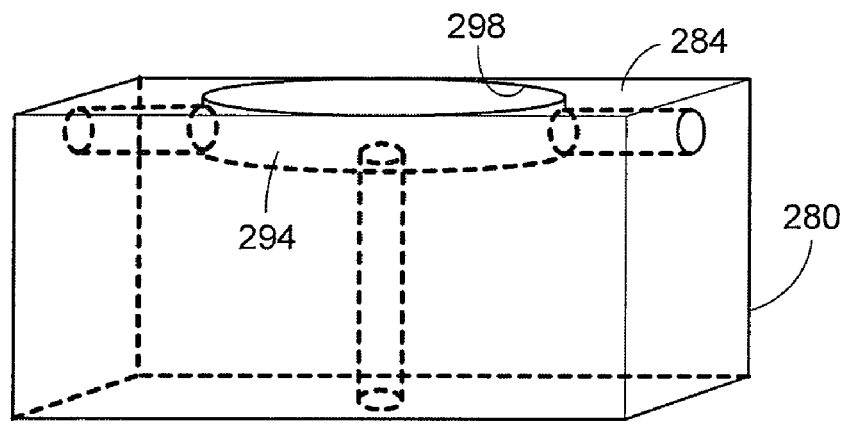
FIG. 13 depicts still another alternate embodiment of the body depicted in FIG. 9.

FIG. 13 depicts a similar embodiment in which a top edge 298 of the reservoir 294 is coplanar with the surface 284 of the body 280. A water-dipping objective lens (not shown) may extend into the reservoir 294 and, in doing so, may be in contact with fluid flowing through the flow path 110, which may eliminate any interfaces between materials of differing refractive indices.

Figure 14:
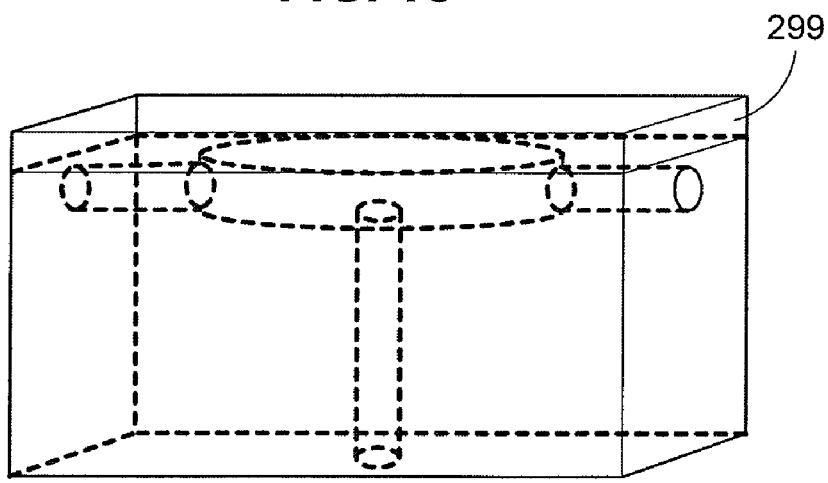
FIG. 14 depicts yet another alternate embodiment of the body depicted in FIG. 9.

FIG. 14 depicts yet another embodiment, in which a coverslip 299 is placed over the exposed reservoir depicted in the embodiment of FIG. 13.

Figure 15:
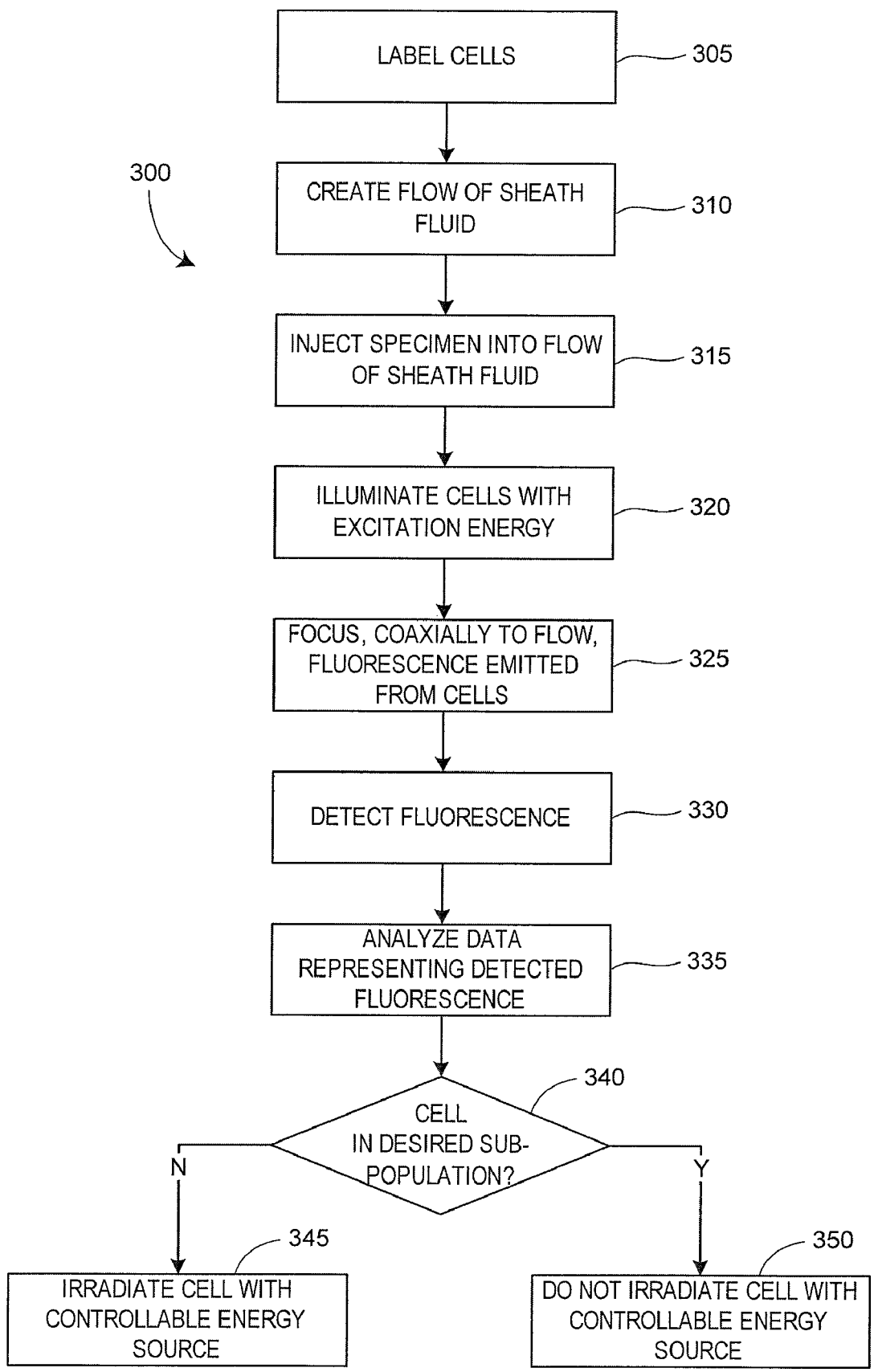
FIG. 15 depicts a flow chart illustrating the steps of a method in accordance with the presently described methods and apparatus.

FIG. 15 illustrates a method 300 of selecting a desired sub-population of cells from a sample of cells. In some embodiments, the method 300, or portions thereof, is stored in a memory as a set of machine-readable instructions making up a control routine for one or more associated apparatus. A processor may read the instructions from the memory and execute the instructions to perform the method 300. In another embodiment, the method 300 includes several routines, which routines may individually control one or more apparatus, may analyze data collected by the one or more apparatus, may make one or more determinations based on the analyzed data, etc. As generally known, a technician or apparatus may label (e.g., by applying a Hoechst stain) a specimen for analysis (e.g., a collection of sperm cells) (block 305). Labeling the cells may be accomplished within a sorting flow cytometer, or in a separate process or procedure outside of the sorting flow cytometer. Moreover, the particular label applied to the cells may depend upon the cytometric application.

In any event, after labeling the cells, a sorting flow cytometer may create a flow of sheath fluid in a flow path (block 310). Through a separate input, the sorting flow cytometer may inject a specimen (i.e., the labeled cells) into the flow path (block 315), preferably at or near the center of the flow of sheath fluid. Also preferably, the specimen enters the flow of sheath fluid slowly relative to the flow of sheath fluid, such that the cells within the specimen (e.g., the sperm cells) align with a long axis parallel to the flow of sheath fluid, and such that the cells flow in a generally single-file pattern.

As the cells move through the flow path, an excitation energy source, such as a UV laser, illuminates the specimen (block 320). The excitation energy source may continually illuminate the flow path, or a routine executing on the processor may control the excitation energy source to illuminate the flow path selectively (e.g., only when a specimen is present in the flow path).

An objective lens or other focusing means operates to focus energy emitted, transmitted, or reflected from each cell (e.g., fluorescent light emitted by the label) in a direction coaxial to the flow (block 325). That is, the combined sheath flow and specimen within the flow path move generally toward an objective lens having an optical axis that is generally coaxial with the flow and, nominally, each cell within the specimen passes through a focal point of the objective lens. A detector receives the focused energy from the objective lens (block 330), and sends a signal representative of the detected energy to a controller. In some embodiments, the detector may detect individually the focused energy from more than 40,000 cells per second, may detect individually the focused energy from more than 75,000 cells per second, or may detect individually the focused energy from more than 100,000 cells per second.

The controller receives the signal representative of the detected energy and analyzes the data (block 335) to determine (at block 340) whether the data represent a cell within the desired sub-population, a cell not within the desired sub-population, or an indeterminate cell which can neither be determined to be in the desired sub-population nor be determined not to be in the desired sub-population. In the latter case, the controller may treat the cell as though the detector determined that the cell was not in desired sub-population. If the controller determines that the cell is not in the desired sub-population or is indeterminate, the controller may send a signal to a controllable energy source, such as an infrared laser, to irradiate the cell (e.g., to alter the cell, destroy the cell, render the cell non-viable, etc.) (block 345). Alternatively, if the controller determines that the cell is in the desired sub-population, the controller may send a signal to the controllable energy source (or refrain from sending a signal) such that the controllable energy source does not irradiate the cell (block 350).

The apparatus may collect the cells for use and/or further processing (e.g., separating the cells) at the end of the process. In some embodiments, which may include the embodiment depicted in FIG. 15, the controller sends a signal to the controllable energy source to leave unaltered (i.e., not to irradiate) cells determined to be in the desired sub-population, and the resulting collection of processed cells comprises a ratio of cells in the desired sub-population of cells to total unaltered cells greater than or equal to 60%. Further, in some embodiments, which may include the embodiment depicted in FIG. 15, the controller sends a signal to the controllable energy source to leave unaltered (i.e., not to irradiate) cells determined to be in the desired sub-population, and the resulting collection of processed cells comprises a ratio of altered cells in the desired sub-population to total cells in the desired sub-population less than or equal to 50%.

Of course, the method described above reflects one or more embodiments of the presently described methods, but may also encompass one or more additional steps or routines, as described throughout this specification with respect to various embodiments. Moreover, some embodiments may omit one or more of the steps or routines described with reference to method 300. By way of example and not limitation, in some embodiments, the label may auto-fluoresce, thereby eliminating the need to illuminate the specimen with an illumination energy source. Further, in some embodiments (as described above), the method may reverse blocks 345 and 350, allowing cells determined not to be in the desired sub-population to pass without irradiation by the controllable energy source, while causing the controllable energy source to irradiate cells determined to be in the desired sub-population.

The methods and apparatus provide a number of important advantages over currently implemented sorting flow cytometers. As one advantage, the presently described methods and apparatus do not subject the analyte cells, which in some embodiments are mammalian sperm cells, to the jet-in-air configuration commonly used in sorting flow cytometers. The result is that a cytometer according to the presently described embodiments does not expose the analyte cells to the environment outside of the cytometer or the resulting collision of the sorted droplet with a receptacle, and do not experience the pressures and pressure changes associated with a nozzle of the jet-in-air configuration. This allows use of the cytometer outside of an environment that implements strict conditions of air quality and temperature control (e.g., outside of a "clean room" environment). In fact, the cytometer itself may implement temperature control to extend the viability of the analyte cells. Moreover, the presently described methods and apparatus may detect and alter the analyte cells faster and/or more accurately, in part because the generally coaxial alignment of the objective lens with the flow of the analyte through the interrogation area mitigates and/or eliminates the problems associated with the anisotropic emission of energy from the analyte, particularly in embodiments used to sort many types of mammalian sperm cells. Having read the present description of the methods and apparatus disclosed herein, other advantages of the presently described methods and apparatus will be apparent to those of ordinary skill in the art.

Although the foregoing text sets forth a detailed description of numerous different embodiments, it should be understood that the scope of protection is defined by the words of the claims to follow. The detailed description is to be construed as exemplary only and does not describe every possible embodiment because describing every possible embodiment would be impractical, if not impossible. Numerous alternative embodiments could be implemented, using either current technology or technology developed after the filing date of this patent, which would still fall within the scope of the claims.

Thus, many modifications and variations may be made in the techniques and structures described and illustrated herein without departing from the spirit and scope of the present claims. Accordingly, it should be understood that the methods and apparatus described herein are illustrative only and are not limiting upon the scope of the claims. The specification above describes at least the following aspects:

1. A method of selecting a first set of cells from a population of cells including the first set of cells and a second set of cells, the method comprising:

labeling the population of cells so that the first set of cells can be distinguished from the second set of cells;

providing a first flow path having a distal end, a proximal end, an interrogation area disposed between the proximal end and the distal end, and a flow axis;

creating a sheath flow of a sheath fluid through the first flow path, the sheath flow moving toward the proximal end at a first flow rate;

injecting into the sheath flow, at a point upstream from the proximal end, a specimen flow including the population of cells, the specimen flow having initially a second flow rate less than the first flow rate;

providing an excitation energy source, the energy emitted from the excitation energy source acting on individual cells as they pass through the interrogation area and causing emission or transmission of secondary radiation from the cells;

using an objective lens having an optical axis generally coaxially aligned with the flow axis to focus the secondary radiation from the individual cells as the cells pass through the interrogation area;

detecting the focused secondary radiation from the individual cells;

determining, from the detected secondary radiation, whether the individual cells are in the first set or the second set; and selecting cells determined to be in the first set.

2. The method of aspect 1, wherein selecting cells determined to be in the first set comprises one of derivatizing, killing, damaging, modifying, disrupting, or fragmenting cells not determined to be in the first set.

3. The method of aspect 1, wherein selecting cells determined to be in the first set comprises ejecting the cells in a stream from a nozzle, creating a plurality of droplets from the stream, selectively applying a charge to the droplets, and sorting the droplets according to the charge of each droplet.

4. The method of any of aspects 1 to 3, wherein labeling the population of cells comprises staining the cells.

5. The method of any of aspects 1 to 4, wherein causing the emission of a secondary radiation comprises causing the emission of fluorescent light.

6. The method of any of aspects 1 to 5, wherein the energy emitted from the excitation energy source passes through the objective lens.

7. The method of any of aspects 1 to 6, wherein the cells are sperm cells and further wherein the first set of cells comprises either cells with an X chromosome or cells with a Y chromosome.

8. The method of any of aspects 1 to 7, wherein selecting cells determined to be in the first set comprises using a differentiation energy source to irradiate cells not determined to be in the first set.

9. The method of aspect 8, wherein the differentiation energy source is a near infrared laser.

10. The method of aspect 8 or aspect 9, wherein the energy emitted from the differentiation energy source passes through the objective lens.

11. The method of any of aspects 1 to 10, wherein providing an excitation energy source comprises providing an ultraviolet laser.

12. The method of aspect 10, further comprising:

selecting a combination of a wavelength of the differentiation energy source, the first flow rate, the second flow rate, and the objective lens such that a nominal focal point of the objective lens and a nominal focal point of the differentiation energy source are separated by the distance that the individual cells will travel through the flow path between detecting the focused secondary radiation and using the differentiation energy source to irradiate cells not determined not to be in the first set.

13. The method of aspect 8 or aspect 10, wherein providing an excitation energy source comprises providing an attenuated output from the differentiation energy source.

14. The method of any of aspects 1 to 13, further comprising providing a second flow path transverse to the flow axis and disposed at the proximal end of the first flow path, such that after passing through the interrogation area and reaching the proximal end of the first flow path, the cells move into the second flow path and away from the interrogation area.

15. The method of any of aspects 1 to 14, wherein providing a flow path further comprises providing a flow path formed of a material having a refractive index in the range of 1.30 to 1.40 inclusive.

16. The method of any of aspects 1 to 15, further comprising adjusting the refractive index of a solution containing the population of cells such that the refractive index of the solution is within 0.02 of the refractive index of the material forming the flow path.

17. An apparatus for detecting and selectively altering a desired sub-population of cells in a population of specimen cells, the apparatus comprising:

a fluid flow path having:
a first flow section having a flow axis, and
a second flow section,
the first and second flow sections intersecting at a measurement end of the first flow section;

an interrogation area disposed at or near the measurement end of the first flow section;

a sheath fluid input in fluid flow communication with the fluid flow path;

a specimen input in fluid flow communication with the fluid flow path;

an objective lens having a nominal focal point and an optical axis, and disposed at the measurement end of the first flow section, the objective lens aligned with the first flow section such that the nominal focal point is along the flow axis and in the interrogation area, and such that the optical axis is generally coaxially aligned with the flow axis;

a detector disposed to detect light focused by the objective lens;

a logic routine communicatively coupled to the detector, operable to determine whether a cell in the population of specimen cells is one of the desired sub-population of cells, and further operable to output a signal based on the determination of whether the cell is one of the desired sub-population of cells; and a controllable energy source communicatively coupled to the logic routine and operable to selectively alter either cells in the desired sub-population of cells or cells not in the desired sub-population of cells according to at least the signal output from the logic routine.

18. The apparatus of aspect 17, wherein the controllable energy source selectively alters cells by derivatizing, killing, damaging, modifying, disrupting, or fragmenting one or more cells not determined to be in the desired sub-population.

19. The apparatus of aspect 17 or aspect 18, further comprising an excitation energy source.

20. The apparatus of aspect 19, wherein energy emitted from the excitation energy source passes through the objective lens.

21. The apparatus of aspect 19 or aspect 20, wherein the excitation energy source comprises an attenuator having the controllable energy source as an input.

22. The apparatus of any of aspects 17 to 21, wherein energy emitted from the controllable energy source passes through the objective lens.

23. The apparatus of any of aspects 17 to 22, wherein the controllable energy source comprises a laser.

24. The apparatus of any of aspects 17 to 23, wherein the controllable energy source comprises a near infrared laser.

25. The apparatus of any of aspects 17 to 24, further comprising a body in which the flow path is formed.

26. The apparatus of aspect 25, further comprising a groove forming the second flow section in a first surface of the body, wherein the measurement end of the first flow section intersects the groove at the first surface.

27. The apparatus of aspect 25, further comprising:

a first interior channel through the body, extending from a first surface of the body to a point in the body and forming the first flow section; and a second interior channel through the body, extending from the point in the body to a second surface of the body.

28. The apparatus of any of aspects 25 to 27, wherein the body is formed of a material having a refractive index between 1.30 and 1.40 inclusive.

29. The apparatus of aspect 28, wherein the material comprises an amorphous perfluoropolymer, an amorphous fluoropolymer, or a perfluoroalkoxy polymer.

30. The apparatus of any of aspects 17 to 29, wherein the objective lens is either a water immersion lens or a water-dipping lens.

31. The apparatus of any of aspects 17 to 30, wherein the population of specimen cells comprises sperm cells.

32. The apparatus of aspect 31, wherein the desired population of cells comprises either cells with an X chromosome or cells with a Y chromosome.

33. A system for detecting and selectively altering a desired sub-population of cells in a population of specimen cells, the system comprising:
fluid flow path having a flow axis;
an interrogation area disposed within the fluid flow path;
a sheath fluid input in fluid flow communication with the fluid flow path;
a first pump in fluid flow communication with the sheath fluid input;
a specimen fluid input in fluid flow communication with the fluid flow path;
a second pump in fluid flow communication with the specimen fluid input;
an objective lens having a nominal focal point and an optical axis, and disposed such that the nominal focal point is along the flow axis and in the interrogation area, and such that the optical axis is generally coaxially aligned with the flow axis in the interrogation area;
a detector disposed to detect light focused by the objective lens;
a controllable energy source;
a processor communicatively coupled to a computer-readable storage medium, to the detector, and to the controllable energy source; and
wherein the processor and the controllable energy source cooperate to selectively alter, according to an output from the processor, either cells in the desired sub-population of cells or cells not in the desired sub-population of cells.

34. The system of aspect 33, further wherein the processor and the controllable energy source cooperate to selectively alter cells in the desired sub-population of cells by derivatizing, killing, damaging, modifying, disrupting, or fragmenting one or more cells not determined to be in the desired sub-population of cells.

35. The system of aspect 33 or aspect 34, wherein the energy emitted from the controllable energy source passes through the objective lens.

36. The system of any of aspects 33 to 35, wherein the controllable energy source comprises a near infrared laser.

37. The system of any of aspects 33 to 35, further comprising a body formed of a material having a refractive index between 1.30 and 1.40 inclusive.

38. The system of any of aspects 33 to 37 wherein the population of specimen cells comprises sperm cells.

39. The system of aspect 38, wherein the desired sub-population is either cells with an X chromosome or cells with a Y chromosome.

40. A method of detecting and selectively altering a desired sub-population of cells in a population of specimen cells, the method embodied in a set of machine-readable instructions executed on a processor and stored on a tangible medium, the method comprising:
controlling the flow of a population of specimen cells through a flow path having a flow axis;
controlling an illumination source to illuminate an interrogation area through which the cells in the population of specimen cells pass;
receiving data from a detector in an optical path having an objective lens, the objective lens having an optical axis and a nominal focal point, the optical axis generally coaxially aligned with the flow axis, the nominal focal point being within the interrogation area;
determining from the received data the presence in the interrogation area of one of the cells in the population of specimen cells;
determining from the received data whether the one of the specimen cells is one of the desired sub-population of cells; and
controlling a cell selection energy source, according to at least the determination of whether the one of the specimen cells is part of the desired sub-population of cells.

41. The method of aspect 40, wherein controlling the cell selection energy source comprises:
determining the rate of flow through the interrogation area of the one of the specimen cells; and
selectively irradiating the one of the cells by controlling the cell selection energy source according to the determined rate of flow of the one of the specimen cells through the flow path.

42. The method of aspect 40, wherein controlling the cell selection energy source comprises selectively applying a charge to a droplet containing a one of the cells.

43. A system for detecting and selectively altering a desired sub-population of cells in a population of specimen cells, the system comprising:
a flow path having an interrogation area and a flow axis in the interrogation area;
control means for controlling a flow of the population of specimen cells through the flow path;
illumination means for illuminating the specimen cells as they pass through the interrogation area;
an objective lens having an optical axis and a nominal focal point, the optical axis generally coaxially aligned with the flow axis, the nominal focal point being within the interrogation area;
detection means for detecting energy focused by the objective lens and providing data related to the detected energy;
processing means for receiving the data related to the detected energy and for determining whether individual specimen cells passing through the interrogation area are one of the desired sub-population;
cell selection means for selectively irradiating the specimen cells; and
cell selection control means for controlling the cell selection means according to at least the determination of whether the individual specimen cells are one of the desired sub-population.

44. The system of aspect 43, wherein the population of specimen cells comprises a population of sperm cells and wherein the desired sub-population of cells comprises sperm cells with an X chromosome.

45. The system of aspect 43, wherein the population of specimen cells comprises a population of sperm cells and wherein the desired sub-population of cells comprises sperm cells with an Y chromosome.

46. The system of any of aspects 43 to 45, wherein energy emitted from the cell selection means passes through the objective lens before reaching the specimen cells.

47. The system of any of aspects 43 to 46, wherein at least a part of the flow path is formed of a material having a refractive index between 1.30 and 1.40 inclusive.

48. A process for detecting and selectively altering a desired sub-population of cells in a population of specimen cells, the process comprising:
   creating a flow carrying a generally single-file procession of specimen cells through a flow path;
   illuminating the specimen cells as the specimen cells pass through an interrogation area in the flow path;
   positioning an objective lens such that:
      an optical axis of the objective lens is generally coaxial with the flow path,
      the flow moves through the flow path toward the objective lens, and
      the objective lens has a nominal focal point in the interrogation area;
   detecting a parameter of individual specimen cells as the specimen cells pass through the interrogation area;
   interpreting the detected parameter of the individual specimen cells to determine whether the individual specimen cells are one of the desired sub-population;
   selectively derivatizing, killing, damaging, modifying, disrupting, or fragmenting one or more of the population of specimen cells according to the determination of whether the individual specimen cells are one of the desired sub-population of cells; and
   collecting the resulting population of processed cells.

49. The process of aspect 48:
   wherein the population of specimen cells comprises sperm cells;
   wherein the desired sub-population of cells comprises either cells having an X chromosome or cells having a Y chromosome; and
   wherein detecting a parameter of the individual specimen cells as the specimen cells pass through the interrogation area comprises detecting the parameter of more than 40,000 specimen cells per second as the cells pass through the interrogation area.

50. The process of aspect 48, wherein detecting a parameter of the individual specimen cells as the specimen cells pass through the interrogation area comprises detecting the parameter of more than 75,000 specimen cells per second as the cells pass through the interrogation area.

51. The process of aspect 48, wherein detecting a parameter of the individual specimen cells as the specimen cells pass through the interrogation area comprises detecting the parameter of more than 100,000 specimen cells per second as the cells pass through the interrogation area.

52. The process of any of aspects 48 to 51, wherein cells determined to be in the desired sub-population are not altered by selectively derivatizing, killing, damaging, modifying, disrupting, or fragmenting the cells, and wherein the resulting population of processed cells comprises a ratio of cells in the desired sub-population of cells to total unaltered cells greater than or equal to 60%.

53. The process of any of aspects 48 to 51, wherein cells determined to be in the desired sub-population are altered by selectively derivatizing, killing, damaging, modifying, disrupting, or fragmenting the cells, and wherein the resulting population of processed cells comprises a ratio of cells in the desired sub-population of cells to total altered cells greater than or equal to 60%.

54. The process of any of aspects 48 to 53, wherein the cells determined to be in the desired sub-population are not altered by selectively derivatizing, killing, damaging, modifying, disrupting, or fragmenting the cells, and wherein the resulting population of processed cells comprises a ratio of altered cells in the desired sub-population to total cells in the desired sub-population less than or equal to 50%.

55. The process of any of aspects 48 to 53, wherein the cells determined to be in the desired sub-population are altered by selectively derivatizing, killing, damaging, modifying, disrupting, or fragmenting the cells, and wherein the resulting population of processes cells comprises a ratio of unaltered cells in the desired sub-population to total cells in the desired sub-population less than or equal to 50%.

I claim:

1. A method of selecting a first set of cells from a population of cells including the first set of cells and a second set of cells, the method comprising:
   labeling the population of cells so that the first set of cells can be distinguished from the second set of cells;
   providing a first flow path having a distal end, a proximal end, an interrogation area disposed between the proximal end and the distal end, and a flow axis;
   creating a sheath flow of a sheath fluid through the first flow path, the sheath flow moving toward the proximal end at a first flow rate;
   injecting into the sheath flow, at a point upstream from the proximal end, a specimen flow including the population of cells, the specimen flow having initially a second flow rate less than the first flow rate;
   providing an excitation energy source, the energy emitted from the excitation energy source acting on individual cells as they pass through the interrogation area and causing emission or transmission of secondary radiation from the cells;
   using an objective lens having an optical axis generally coaxially aligned with the flow axis to focus the secondary radiation from the individual cells as the cells pass through the interrogation area;
   detecting the focused secondary radiation from the individual cells;
   determining, from the detected secondary radiation, whether the individual cells are in the first set or the second set; and
   selecting cells determined to be in the first set.

2. The method of claim 1, wherein selecting cells determined to be in the first set comprises one of derivatizing, killing, damaging, modifying, disrupting, or fragmenting cells not determined to be in the first set.

3. The method of claim 1, wherein selecting cells determined to be in the first set comprises:
   ejecting the cells in a stream from a nozzle;
   creating a plurality of droplets from the stream;
   selectively applying a charge to the droplets; and
   sorting the droplets according to the charge of each droplet.

4. The method of claim 1, wherein the energy emitted from the excitation energy source passes through the objective lens.

5. The method of claim 1, wherein the cells are sperm cells and further wherein the first set of cells comprises either cells with an X chromosome or cells with a Y chromosome.

6. The method of claim 1, wherein selecting cells determined to be in the first set comprises using a differentiation energy source to irradiate cells not determined to be in the first set.

7. The method of claim 6, wherein the energy emitted from the differentiation energy source passes through the objective lens.

8. The method of claim 7, further comprising:
selecting a combination of a wavelength of the differentiation energy source, the first flow rate, the second flow rate, and the objective lens such that a nominal focal point of the objective lens and a nominal focal point of the differentiation energy source are separated by the distance that the individual cells will travel through the flow path between detecting the focused secondary radiation and using the differentiation energy source to irradiate cells not determined not to be in the first set.

9. The method of claim 1, further comprising providing a second flow path transverse to the flow axis and disposed at the proximal end of the first flow path, such that after passing through the interrogation area and reaching the proximal end of the first flow path, the cells move into the second flow path and away from the interrogation area.

10. The method of claim 1, wherein providing a flow path further comprises providing a flow path formed of a material having a refractive index in the range of 1.30 to 1.40 inclusive.

11. The method of claim 1, further comprising adjusting the refractive index of a solution containing the population of cells such that the refractive index of the solution is within 0.02 of the refractive index of a material forming the flow path.

12. An apparatus for detecting and selectively altering a desired sub-population of cells in a population of specimen cells, the apparatus comprising:
a fluid flow path having:
a first flow section having a flow axis, and
a second flow section,
the first and second flow sections intersecting at a measurement end of the first flow section;
an interrogation area disposed at or near the measurement end of the first flow section;
a sheath fluid input in fluid flow communication with the fluid flow path;
a specimen input in fluid flow communication with the fluid flow path;
an objective lens having a nominal focal point and an optical axis, and disposed at the measurement end of the first flow section, the objective lens aligned with the first flow section such that the nominal focal point is along the flow axis and in the interrogation area, and such that the optical axis is generally coaxially aligned with the flow axis;
a detector disposed to detect light focused by the objective lens;
a logic routine communicatively coupled to the detector, operable to determine whether a cell in the population of specimen cells is one of the desired sub-population of cells, and further operable to output a signal based on the determination of whether the cell is one of the desired sub-population of cells; and
a controllable energy source communicatively coupled to the logic routine and operable to selectively alter either cells in the desired sub-population of cells or cells not in the desired sub-population of cells according to at least the signal output from the logic routine.

13. The apparatus of claim 12, wherein the controllable energy source selectively alters cells by derivatizing, killing, damaging, modifying, disrupting, or fragmenting one or more cells not determined to be in the desired sub-population.

14. The apparatus of claim 12, further comprising an excitation energy source and wherein energy emitted from the excitation source passes through the objective lens.

15. The apparatus of claim 14, wherein the excitation energy source comprises an attenuator having the controllable energy source as an input.

16. The apparatus of claim 12, wherein energy emitted from the controllable energy source passes through the objective lens.

17. The apparatus of claim 12, further comprising a body in which the flow path is formed.

18. The apparatus of claim 17, further comprising a groove forming the second flow section in a first surface of the body, wherein the measurement end of the first flow section intersects the groove at the first surface.

19. The apparatus of claim 17, further comprising:
a first interior channel through the body, extending from a first surface of the body to a point in the body and forming the first flow section; and
a second interior channel through the body, extending from the point in the body to a second surface of the body.

20. The apparatus of claim 17, wherein the body is formed of a material having a refractive index between 1.30 and 1.40 inclusive.

21. The apparatus of claim 20, wherein the material comprises an amorphous perfluoropolymer, an amorphous fluoropolymer, or a perfluoroalkoxy polymer.

22. The apparatus of claim 12, wherein the objective lens is either a water immersion lens or a water-dipping lens.

23. The apparatus of claim 12, wherein the population of specimen cells comprises sperm cells and wherein the desired population of cells comprises either cells with an X chromosome or cells with a Y chromosome.

24. A system for detecting and selectively altering a desired sub-population of cells in a population of specimen cells, the system comprising:
fluid flow path having a flow axis;
an interrogation area disposed within the fluid flow path;
a sheath fluid input in fluid flow communication with the fluid flow path;
a first pump in fluid flow communication with the sheath fluid input;
a specimen fluid input in fluid flow communication with the fluid flow path;
a second pump in fluid flow communication with the specimen fluid input;
an objective lens having a nominal focal point and an optical axis, and disposed such that the nominal focal point is along the flow axis and in the interrogation area, and such that the optical axis is generally coaxially aligned with the flow axis in the interrogation area;
a detector disposed to detect light focused by the objective lens;
a controllable energy source;
a processor communicatively coupled to a computer-readable storage medium, to the detector, and to the controllable energy source; and
wherein the processor and the controllable energy source cooperate to selectively alter, according to an output from the processor, either cells in the desired sub-population of cells or cells not in the desired sub-population of cells.

25. The system of claim 24, further wherein the processor and the controllable energy source cooperate to selectively alter cells in the desired sub-population of cells by derivatizing, killing, damaging, modifying, disrupting, or fragmenting one or more cells not determined to be in the desired sub-population of cells.

26. The system of claim 24, wherein the energy emitted from the controllable energy source passes through the objective lens.

27. The system of claim 24, further comprising a body formed of a material having a refractive index between 1.30 and 1.40 inclusive.

28. The system of claim 24, wherein the population of specimen cells comprises sperm cells and wherein the desired sub-population is either cells with an X chromosome or cells with a Y chromosome.

29. A method of detecting and selectively altering a desired sub-population of cells in a population of specimen cells, the method embodied in a set of machine-readable instructions executed on a processor and stored on a tangible medium, the method comprising:
   controlling the flow of a population of specimen cells through a flow path having a flow axis;
   controlling an illumination source to illuminate an interrogation area through which the cells in the population of specimen cells pass;
   receiving data from a detector in an optical path having an objective lens, the objective lens having an optical axis and a nominal focal point, the optical axis generally coaxially aligned with the flow axis, the nominal focal point being within the interrogation area;
   determining from the received data the presence in the interrogation area of one of the cells in the population of specimen cells;
   determining from the received data whether the one of the specimen cells is one of the desired sub-population of cells; and
   controlling a cell selection energy source, according to at least the determination of whether the one of the specimen cells is part of the desired sub-population of cells.

30. The method of claim 29, wherein controlling the cell selection energy source comprises:
   determining the rate of flow through the interrogation area of the one of the specimen cells; and
   selectively irradiating the one of the cells by controlling the cell selection energy source according to the determined rate of flow of the one of the specimen cells through the flow path.

31. The method of claim 29, wherein controlling the cell selection energy source comprises selectively applying a charge to a droplet containing a one of the cells.

32. A system for detecting and selectively altering a desired sub-population of cells in a population of specimen cells, the system comprising:
   a flow path having an interrogation area and a flow axis in the interrogation area;
   control means for controlling a flow of the population of specimen cells through the flow path;
   illumination means for illuminating the specimen cells as they pass through the interrogation area;
   an objective lens having an optical axis and a nominal focal point, the optical axis generally coaxially aligned with the flow axis, the nominal focal point being within the interrogation area;
   detection means for detecting energy focused by the objective lens and providing data related to the detected energy;
   processing means for receiving the data related to the detected energy and for determining whether individual specimen cells passing through the interrogation area are one of the desired sub-population;
   cell selection means for selectively irradiating the specimen cells; and
   cell selection control means for controlling the cell selection means according to at least the determination of whether the individual specimen cells are one of the desired sub-population.

33. The system of claim 32, wherein the population of specimen cells comprises a population of sperm cells and wherein the desired sub-population of cells comprises:
   sperm cells with an X chromosome; or
   sperm cells with a Y chromosome.

34. The system of claim 32, wherein energy emitted from the cell selection means passes through the objective lens before reaching the specimen cells.

35. The system of claim 32, wherein at least a part of the flow path is formed of a material having a refractive index between 1.30 and 1.40 inclusive.

36. A process for detecting and selectively altering a desired sub-population of cells in a population of specimen cells, the process comprising:
   creating a flow carrying a generally single-file procession of specimen cells through a flow path;
   illuminating the specimen cells as the specimen cells pass through an interrogation area in the flow path;
   positioning an objective lens such that:
      an optical axis of the objective lens is generally coaxial with the flow path,
      the flow moves through the flow path toward the objective lens, and
      the objective lens has a nominal focal point in the interrogation area;
   detecting a parameter of individual specimen cells as the specimen cells pass through the interrogation area;
   interpreting the detected parameter of the individual specimen cells to determine whether the individual specimen cells are one of the desired sub-population;
   selectively derivatizing, killing, damaging, modifying, disrupting, or fragmenting one or more of the population of specimen cells according to the determination of whether the individual specimen cells are one of the desired sub-population of cells; and
   collecting the resulting population of processed cells.

37. The process of claim 36:
   wherein the population of specimen cells comprises sperm cells;
   wherein the desired sub-population of cells comprises either cells having an X chromosome or cells having a Y chromosome; and
   wherein detecting a parameter of the individual specimen cells as the specimen cells pass through the interrogation area comprises detecting the parameter of more than 40,000 specimen cells per second as the cells pass through the interrogation area.

38. The process of claim 36, wherein detecting a parameter of the individual specimen cells as the specimen cells pass through the interrogation area comprises detecting the parameter of more than 75,000 specimen cells per second as the cells pass through the interrogation area.

39. The process of claim 36, wherein detecting a parameter of the individual specimen cells as the specimen cells pass through the interrogation area comprises detecting the parameter of more than 100,000 specimen cells per second as the cells pass through the interrogation area.

40. The process of claim 36, wherein cells determined to be in the desired sub-population are not altered by selectively derivatizing, killing, damaging, modifying, disrupting, or fragmenting the cells, and wherein the resulting population of processed cells comprises a ratio of cells in the desired sub-population of cells to total unaltered cells greater than or equal to 60%.

41. The process of claim 36, wherein cells determined to be in the desired sub-population are altered by selectively derivatizing, killing, damaging, modifying, disrupting, or fragmenting the cells, and wherein the resulting population of processed cells comprises a ratio of cells in the desired sub-population of cells to total altered cells greater than or equal to 60%.

42. The process of claim 36, wherein the cells determined to be in the desired sub-population are not altered by selectively derivatizing, killing, damaging, modifying, disrupting, or fragmenting the cells, and wherein the resulting population of processed cells comprises a ratio of altered cells in the desired sub-population to total cells in the desired sub-population less than or equal to 50%.

43. The process of claim 36, wherein the cells determined to be in the desired sub-population are altered by selectively derivatizing, killing, damaging, modifying, disrupting, or fragmenting the cells, and wherein the resulting population of processes cells comprises a ratio of unaltered cells in the desired sub-population to total cells in the desired sub-population less than or equal to 50%.

* * * * *

(12) INTER PARTES REEXAMINATION CERTIFICATE (0408th)
United States Patent
Luscher

(10) Number: US 8,004,661 C1
(45) Certificate Issued: Jul. 17, 2012

(54) METHOD AND APPARATUS FOR SORTING CELLS

(75) Inventor: Mark Luscher, Toronto (CA)

(73) Assignee: Microbix Biosystems Inc., Mississauga (CA)

Reexamination Request:
No. 95/000,643, Oct. 12, 2011

Reexamination Certificate for:
Patent No.: 8,004,661
Issued: Aug. 23, 2011
Appl. No.: 12/495,406
Filed: Jun. 30, 2009

Related U.S. Application Data

(60) Provisional application No. 61/077,083, filed on Jun. 30, 2008.

(51) Int. Cl.
*G01N 21/64* (2006.01)
*C12M 1/42* (2006.01)
*C12M 1/34* (2006.01)

(52) U.S. Cl. ............ 356/72; 356/318; 356/339; 356/342; 356/419; 422/82.08; 435/288.7; 436/172

(58) Field of Classification Search .................. None
See application file for complete search history.

(56) References Cited

To view the complete listing of prior art documents cited during the proceeding for Reexamination Control Number 95/000,643, please refer to the USPTO's public Patent Application Information Retrieval (PAIR) system under the Display References tab.

*Primary Examiner* — Christina Y Leung

(57) ABSTRACT

A method, apparatus, and system for a sorting flow cytometer include an objective lens having an optical axis coaxially aligned with the flow path at the focal point. A controllable energy source selectively alters an analyte according to a determination of whether the analyte is in a desired subpopulation. In various embodiments, one or both or the emission from the controller energy source and/or the emission from an illumination energy source passes through the objective lens. In some embodiments in which the emission from the controllable energy source passes through the objective lens, the objective lens may focus the emission from the controllable energy source at a different point than the focal point of a signal detected from the analyte and, in particular, at a point closer to the objective lens.

At the time of issuance and publication of this certificate, the patent remains subject to pending reexamination control number 90/009,985 filed 2/13/2012. The claim content of the patent may be subsequently revised if a reexamination certificate issues from the reexamination proceeding.

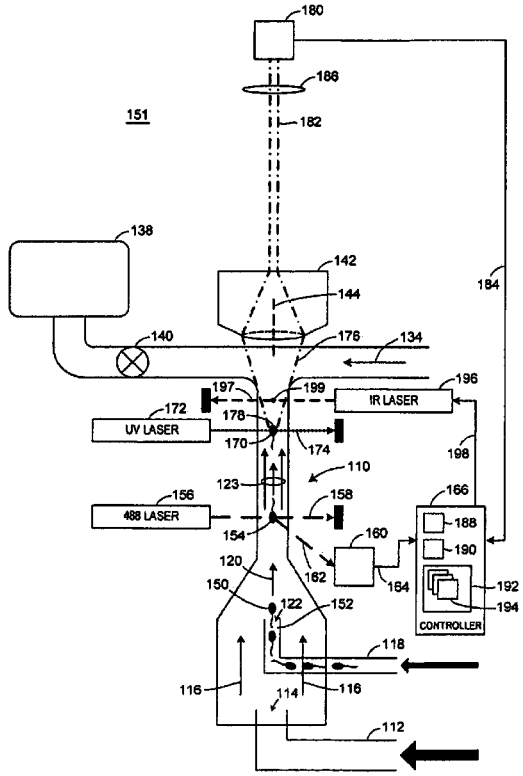

INTER PARTES REEXAMINATION CERTIFICATE ISSUED UNDER 35 U.S.C. 316

THE PATENT IS HEREBY AMENDED AS INDICATED BELOW.

AS A RESULT OF REEXAMINATION, IT HAS BEEN DETERMINED THAT:

Claims 12-14, 16-21, 23-28 and 36-43 are cancelled.
Claims 1-11, 15, 22 and 29-35 were not reexamined.

* * * * *

US 8,004,661 C2

(12) EX PARTE REEXAMINATION CERTIFICATE (9559th)
United States Patent
Luscher

(10) Number: US 8,004,661 C2
(45) Certificate Issued: Mar. 12, 2013

(54) METHOD AND APPARATUS FOR SORTING CELLS

(75) Inventor: Mark Luscher, Toronto (CA)

(73) Assignee: Microbix Biosystems Inc., Mississauga (CA)

Reexamination Request:
No. 90/009,985, Feb. 13, 2012

Reexamination Certificate for:
Patent No.: 8,004,661
Issued: Aug. 23, 2011
Appl. No.: 12/495,406
Filed: Jun. 30, 2009

Reexamination Certificate C1 8,004,661 issued Jul. 17, 2012

Related U.S. Application Data

(60) Provisional application No. 61/077,083, filed on Jun. 30, 2008.

(51) Int. Cl.
    G01N 21/64 (2006.01)
    C12M 1/42 (2006.01)
    C12M 1/34 (2006.01)
(52) U.S. Cl. ....... 356/72; 250/461.2; 356/318; 356/339; 356/342; 356/419; 422/82.08; 435/288.7; 436/172
(58) Field of Classification Search .................. None
    See application file for complete search history.

(56) References Cited

To view the complete listing of prior art documents cited during the proceeding for Reexamination Control Number 90/009,985, please refer to the USPTO's public Patent Application Information Retrieval (PAIR) system under the Display References tab.

Primary Examiner — Christina Y Leung

(57) ABSTRACT

A method, apparatus, and system for a sorting flow cytometer include an objective lens having an optical axis coaxially aligned with the flow path at the focal point. A controllable energy source selectively alters an analyte according to a determination of whether the analyte is in a desired subpopulation. In various embodiments, one or both or the emission from the controller energy source and/or the emission from an illumination energy source passes through the objective lens. In some embodiments in which the emission from the controllable energy source passes through the objective lens, the objective lens may focus the emission from the controllable energy source at a different point than the focal point of a signal detected from the analyte and, in particular, at a point closer to the objective lens.

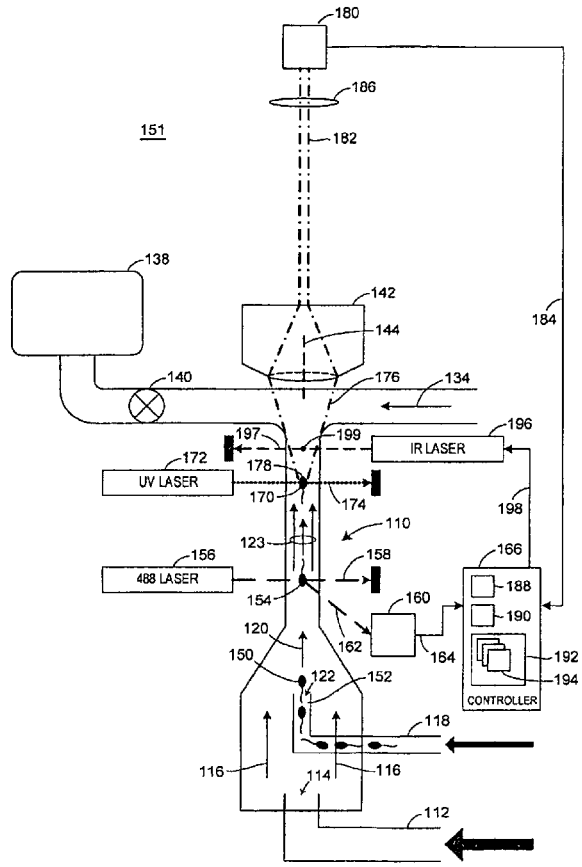

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 1-11 and 29-35 is confirmed.

Claims 15 and 22 are determined to be patentable as amended.

Claims 12-14, 16-21, 23-28 and 36-43 were not reexamined.

15. [The apparatus of claim 14,] *An apparatus for detecting and selectively altering a desired sub-population of cells in a population of specimen cells, the apparatus comprising:*
  *a fluid flow path having:*
    *a first flow section having a flow axis, and a second flow section, the first and second flow sections intersecting at a measurement end of the first flow section;*
    *an interrogation area disposed at or near the measurement end of the first flow section;*
    *a sheath fluid input in fluid flow communication with the fluid flow path; and*
    *a specimen input in fluid flow communication with the fluid flow path;*
  *an objective lens having a nominal focal point and an optical axis, and disposed at the measurement end of the first flow section, the objective lens aligned with the first flow section such that the nominal focal point is along the flow axis and in the interrogation area, and such that the optical axis is generally coaxially aligned with the flow axis;*
  *a detector disposed to detect light focused by the objective lens;*
  *an excitation energy source and wherein energy emitted from the excitation source passes through the objective lens;*
  *a logic routine communicatively coupled to the detector, operable to determine whether a cell in the population of specimen cells is one of the desired sub-population of cells, and further operable to output a signal based on the determination of whether the cell is one of the desired sub-population of cells; and*
  *a controllable energy source communicatively coupled to the logic routine and operable to selectively alter either cells in the desired sub-population of cells or cells not in the desired sub-population of cells according to at least the signal output from the logic routine,*
  wherein the excitation energy source comprises an attenuator having the controllable energy source as an input.

22. [The apparatus of claim 12,] *An apparatus for detecting and selectively altering a desired sub-population of cells in a population of specimen cells, the apparatus comprising:*
  *a fluid flow path having:*
    *a first flow section having a flow axis, and a second flow section, the first and second flow sections intersecting at a measurement end of the first flow section;*
    *an interrogation area disposed at or near the measurement end of the first flow section;*
    *a sheath fluid input in fluid flow communication with the fluid flow path; and*
    *a specimen input in fluid flow communication with the fluid flow path;*
  *an objective lens having a nominal focal point and an optical axis, and disposed at the measurement end of the first flow section, the objective lens aligned with the first flow section such that the nominal focal point is along the flow axis and in the interrogation area, and such that the optical axis is generally coaxially aligned with the flow axis;*
  *a detector disposed to detect light focused by the objective lens;*
  *a logic routine communicatively coupled to the detector, operable to determine whether a cell in the population of specimen cells is one of the desired sub-population of cells, and further operable to output a signal based on the determination of whether the cell is one of the desired sub-population of cells; and*
  *a controllable energy source communicatively coupled to the logic routine and operable to selectively alter either cells in the desired sub-population of cells or cells not in the desired sub-population of cells according to at least the signal output from the logic routine,*
  wherein the objective lens is either a water immersion lens or a water-dipping lens.

\* \* \* \* \*